(12) United States Patent
Buehlmann et al.

(10) Patent No.: US 11,759,193 B2
(45) Date of Patent: Sep. 19, 2023

(54) RETRACTOR MEMBERS, AND RELATED SYSTEMS AND METHODS

(71) Applicant: Medos International Sarl, Le Locle (CH)

(72) Inventors: Eric Buehlmann, Duxbury, MA (US); Clara Cheung, Quincy, MA (US); Thomas Gamache, Westport, MA (US); Roman Lomeli, Plymouth, MA (US); Paul S. Maguire, Hope Valley, RI (US); James Paiva, Warren, RI (US); Joern Richter, Kandern (DE); Daniel Thommen, Liestal (CH); John C. Voellmicke, Franklin, MA (US)

(73) Assignee: Medos International Sarl

( * ) Notice: Subject to any disclaimer, the term of this patent is extended or adjusted under 35 U.S.C. 154(b) by 516 days.

(21) Appl. No.: 16/722,480

(22) Filed: Dec. 20, 2019

(65) Prior Publication Data

US 2021/0186477 A1    Jun. 24, 2021

(51) Int. Cl.
*A61B 17/02* (2006.01)
*A61B 17/00* (2006.01)

(52) U.S. Cl.
CPC ........ *A61B 17/0218* (2013.01); *A61B 17/025* (2013.01); *A61B 2017/0003* (2013.01); *A61B 2017/00407* (2013.01); *A61B 2017/00469* (2013.01); *A61B 2017/00477* (2013.01); *A61B 2017/00561* (2013.01); *A61B 2017/00876* (2013.01); *A61B 2017/00929* (2013.01); *A61B 2017/0225* (2013.01); *A61B 2017/0256* (2013.01)

(58) Field of Classification Search
CPC .... A61B 17/02; A61B 17/0218; A61B 17/025
See application file for complete search history.

(56) References Cited

U.S. PATENT DOCUMENTS

| | | | |
|---|---|---|---|
| 7,198,598 B2 | 4/2007 | Smith et al. | |
| 8,622,897 B2 | 1/2014 | Raymond et al. | |
| 8,998,807 B2 | 4/2015 | Fiorella | |
| 9,615,818 B2 | 4/2017 | Baudouin et al. | |
| 9,795,367 B1 * | 10/2017 | Lee | A61B 1/32 |
| 9,867,605 B2 | 1/2018 | Adams | |

(Continued)

OTHER PUBLICATIONS

U.S. Appl. No. 16/692,342, filed Nov. 22, 2019, entitled Control Member for Adjusting Access Tube Position, and Related Systems and Methods.

*Primary Examiner* — Christopher J Beccia
(74) *Attorney, Agent, or Firm* — BakerHostetler

(57) ABSTRACT

A retractor member is configured for insertion through a channel of an access member and for moving soft tissue at a treatment site that is accessible through the channel. The retractor includes a body having a proximal end and a distal end and spaced from each other along a longitudinal direction. The distal end defines a retractor blade and the body defines a first surface and a second surface opposite each other along a transverse direction substantially perpendicular to the longitudinal direction. The retractor includes an attachment device configured to selectively attach the body to a portion of the access member such that the body is extendable through the working channel while the body is attached to the portion of the access member.

21 Claims, 27 Drawing Sheets

(56) References Cited

U.S. PATENT DOCUMENTS

| | | |
|---|---|---|
| 10,869,660 B2 * | 12/2020 | Berry ................. A61B 17/0293 |
| 2004/0002629 A1 | 1/2004 | Branch et al. |
| 2005/0137461 A1 * | 6/2005 | Marchek .............. A61B 17/025 |
| | | 600/220 |
| 2005/0137609 A1 | 6/2005 | Guiraudon |
| 2006/0200186 A1 * | 9/2006 | Marchek ............ A61B 17/0218 |
| | | 606/191 |
| 2007/0038033 A1 | 2/2007 | Jones et al. |
| 2008/0161650 A1 | 7/2008 | Hestad et al. |
| 2008/0214898 A1 * | 9/2008 | Warren .................. A61B 17/02 |
| | | 600/210 |
| 2018/0008253 A1 | 1/2018 | Thommen et al. |
| 2018/0153592 A1 | 6/2018 | Larson |
| 2019/0183476 A1 | 6/2019 | Garcia-Bengochea et al. |
| 2019/0209154 A1 | 7/2019 | Richter et al. |
| 2020/0245856 A1 * | 8/2020 | Berry ....................... A61B 1/32 |

* cited by examiner

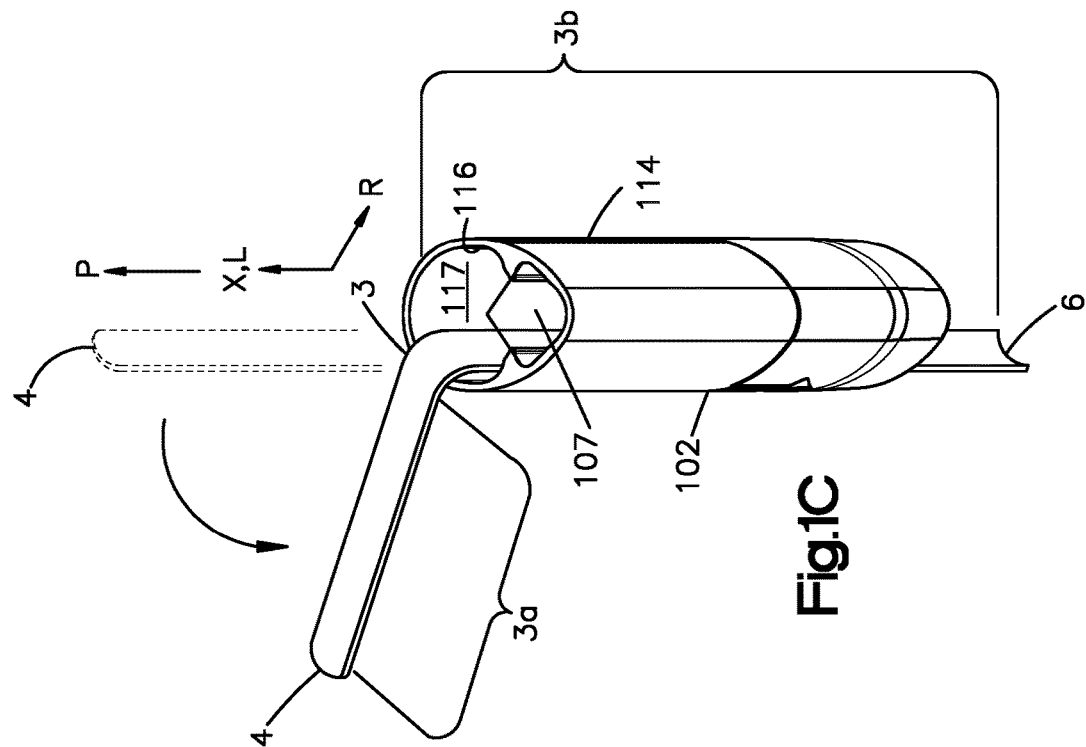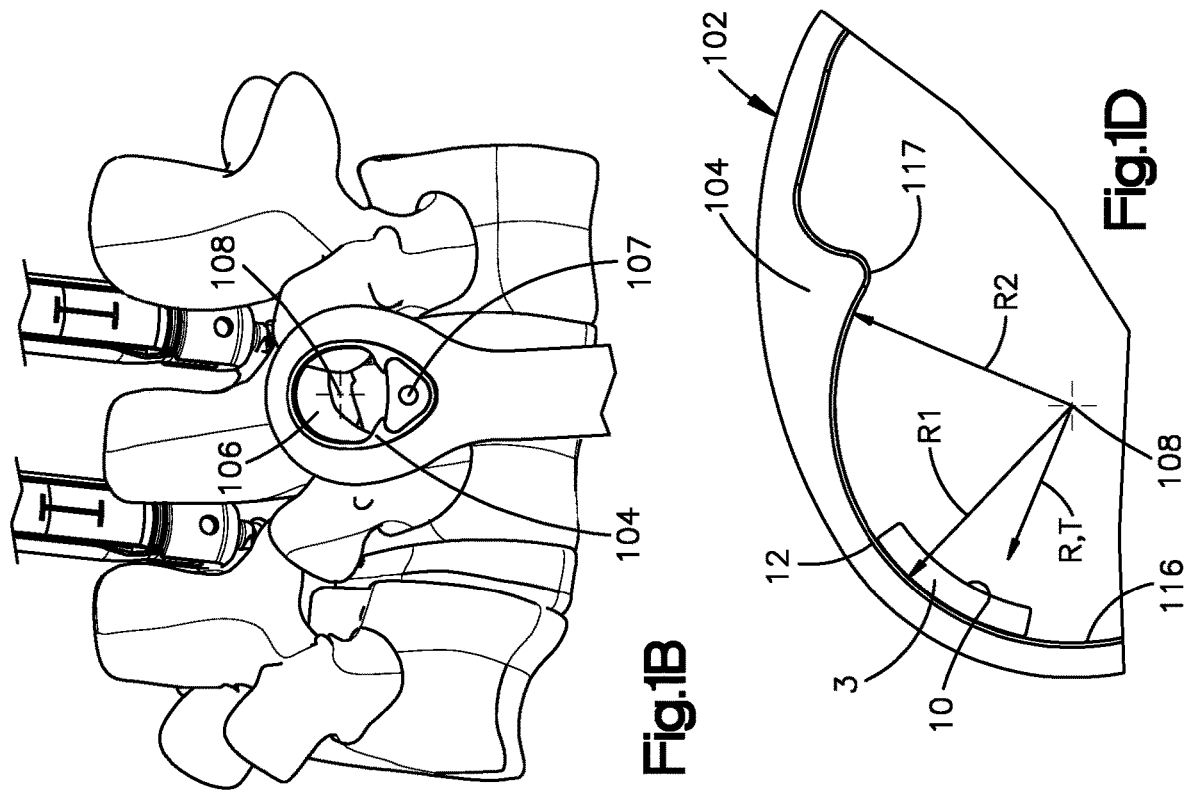

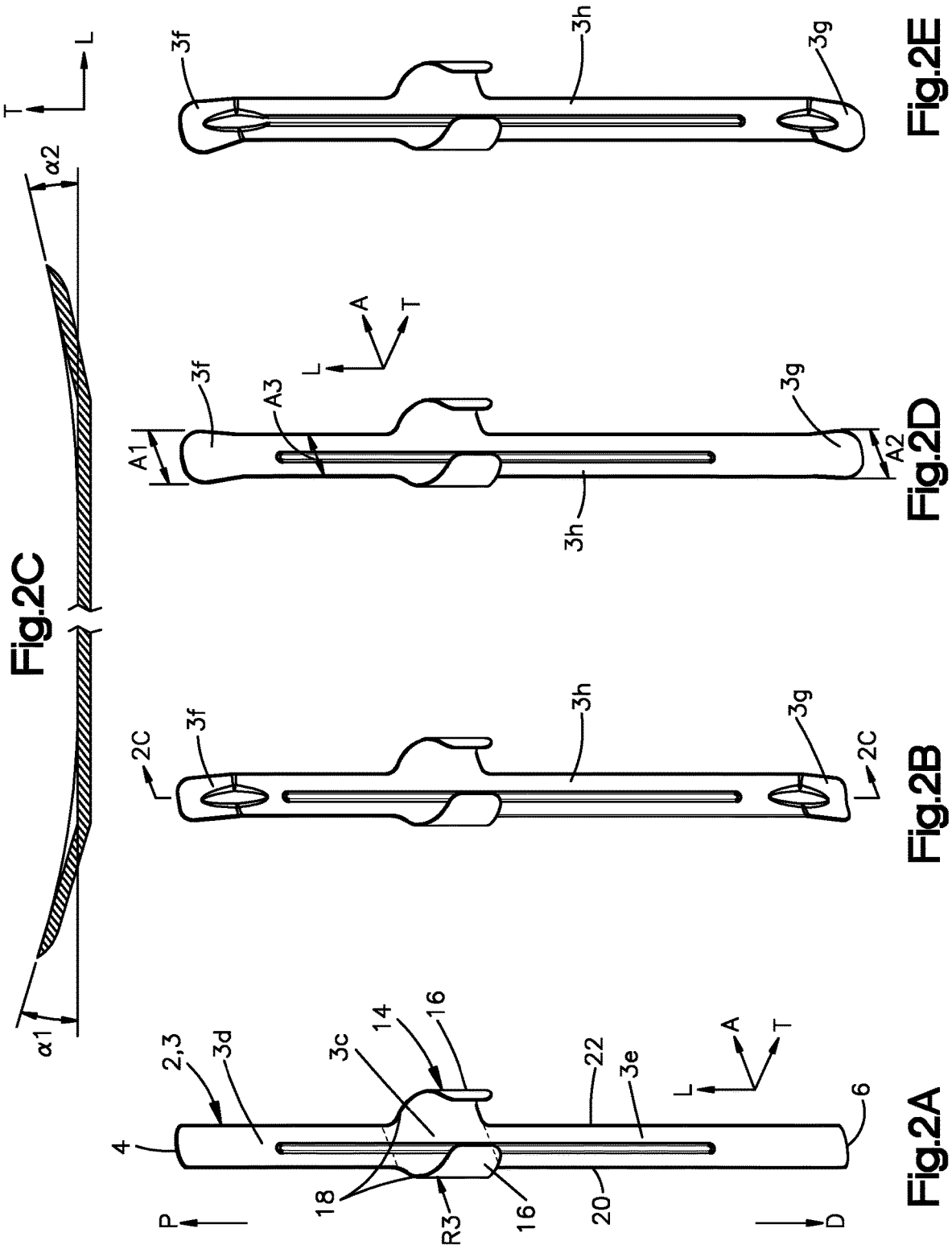

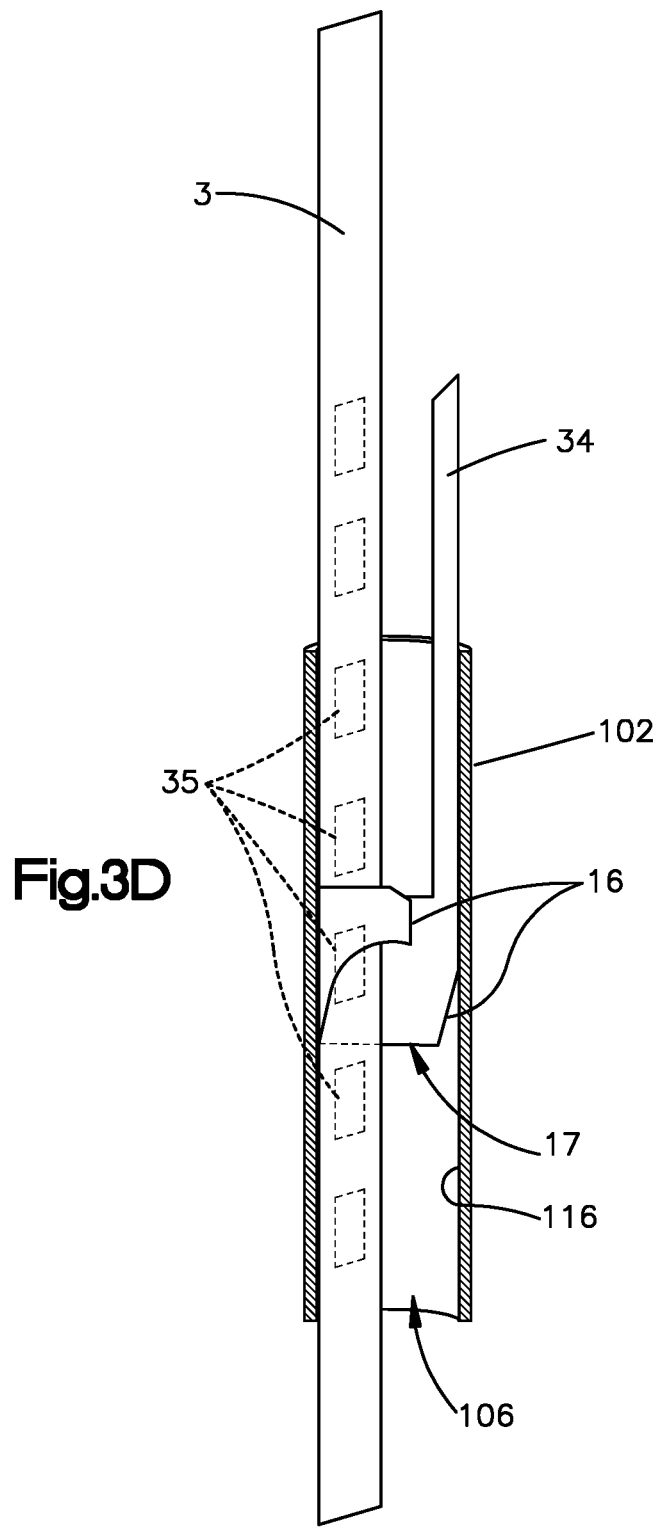

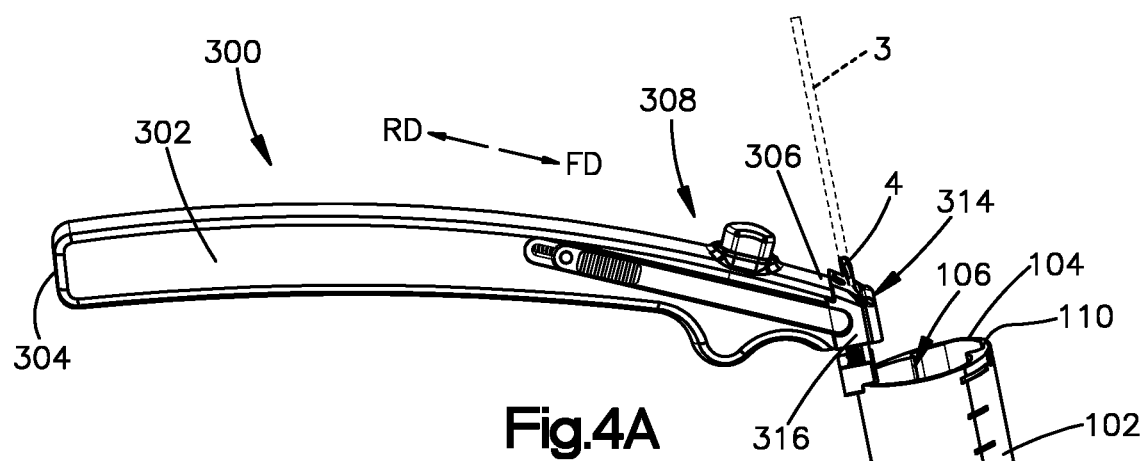
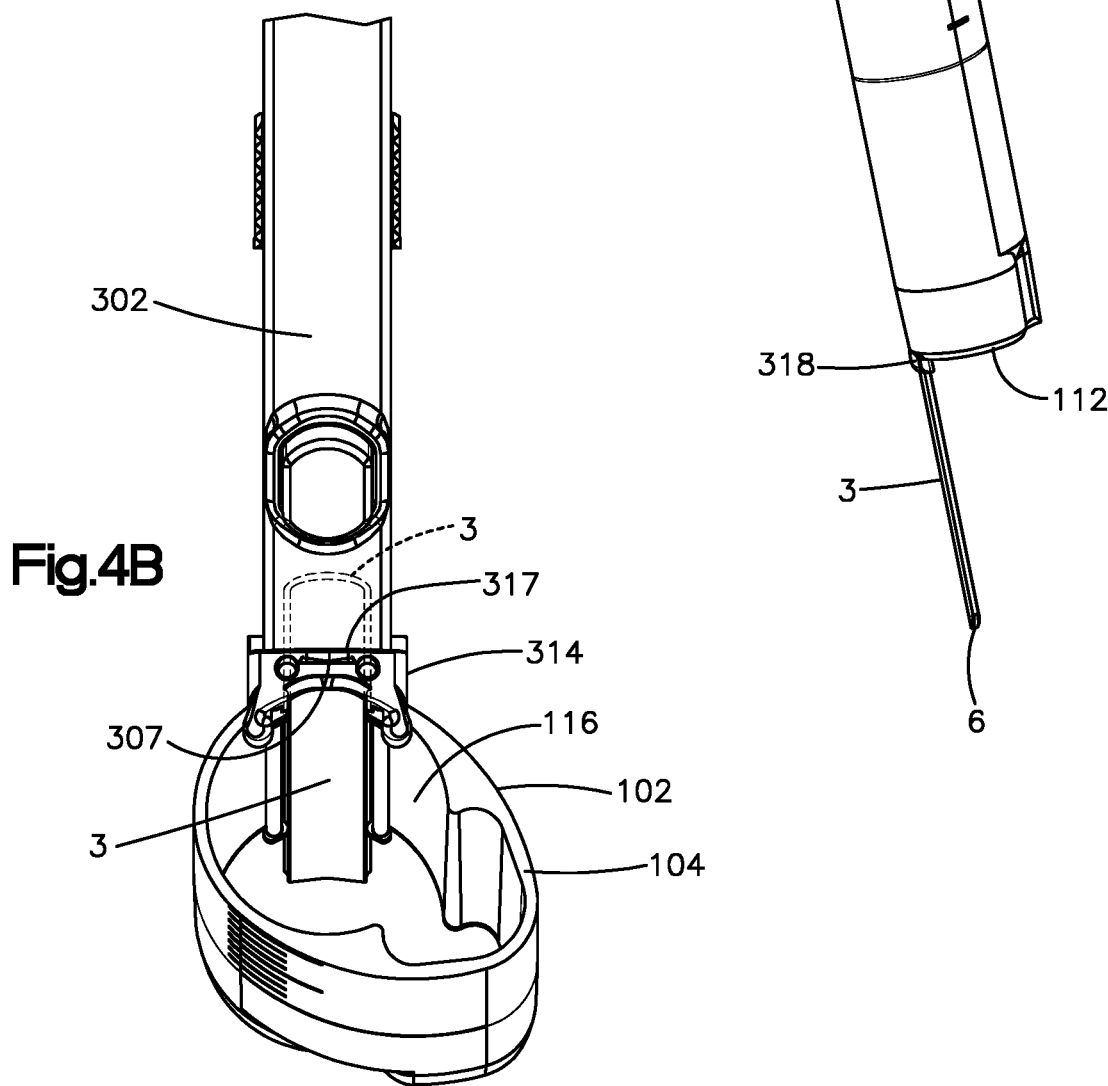

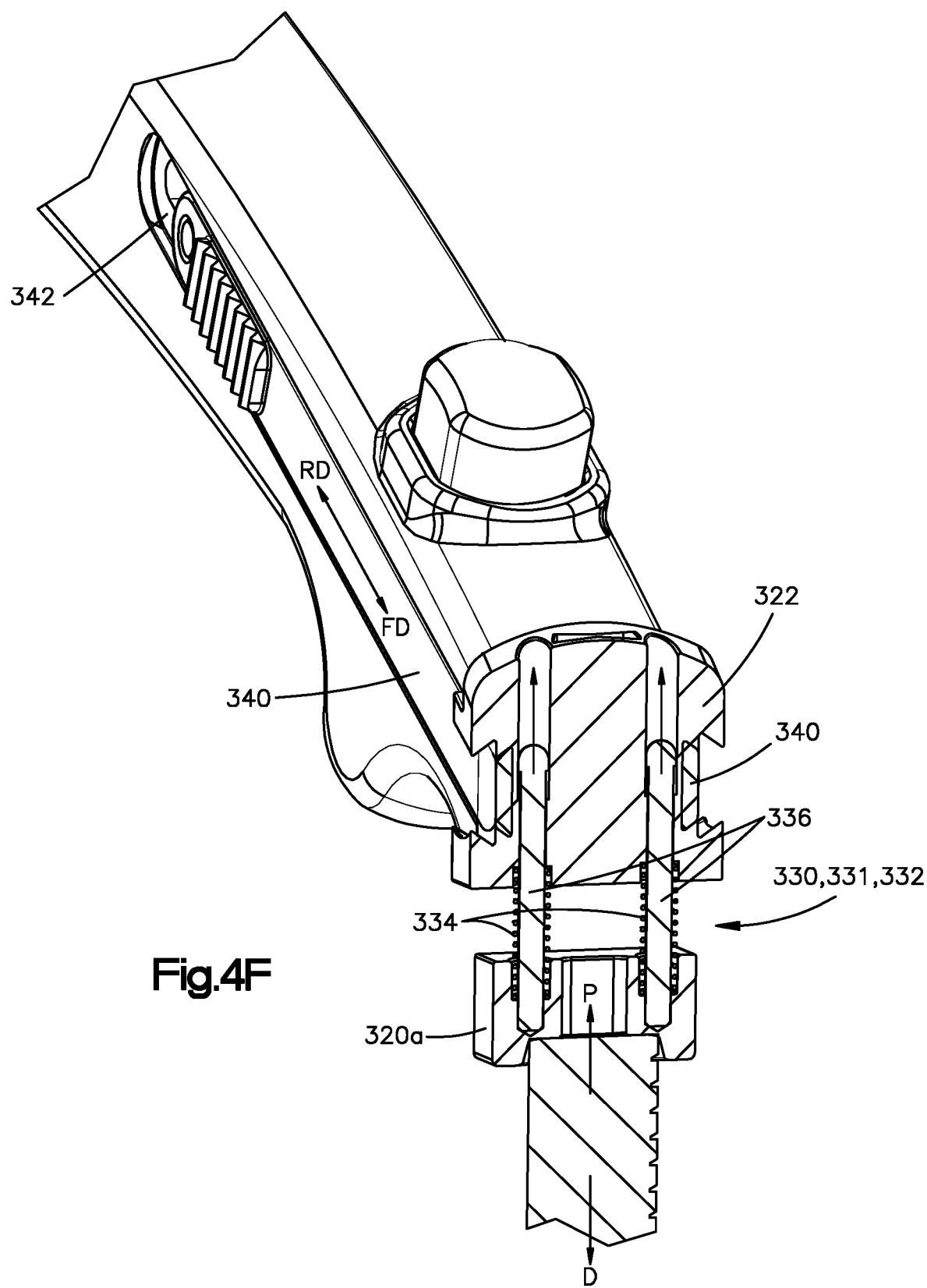

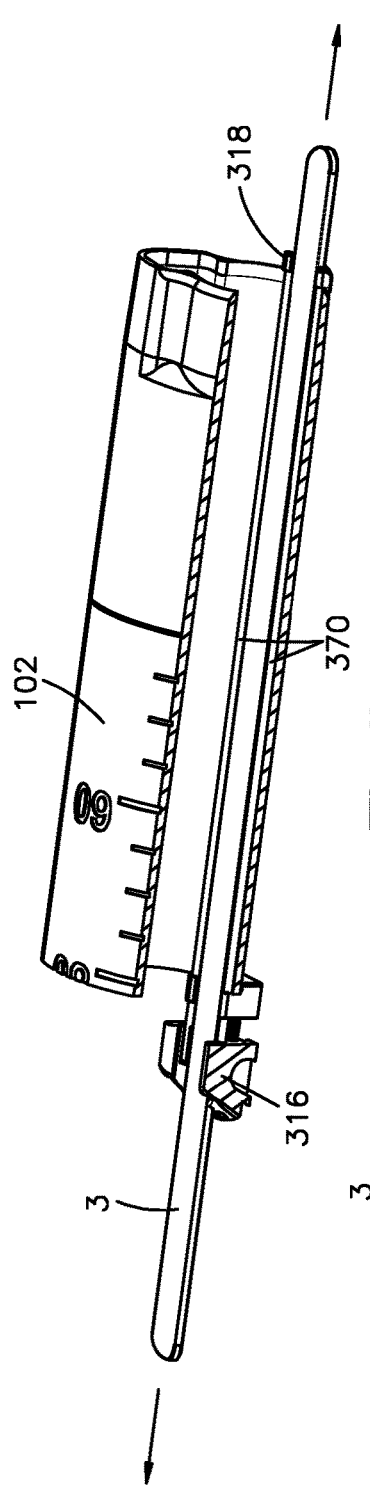
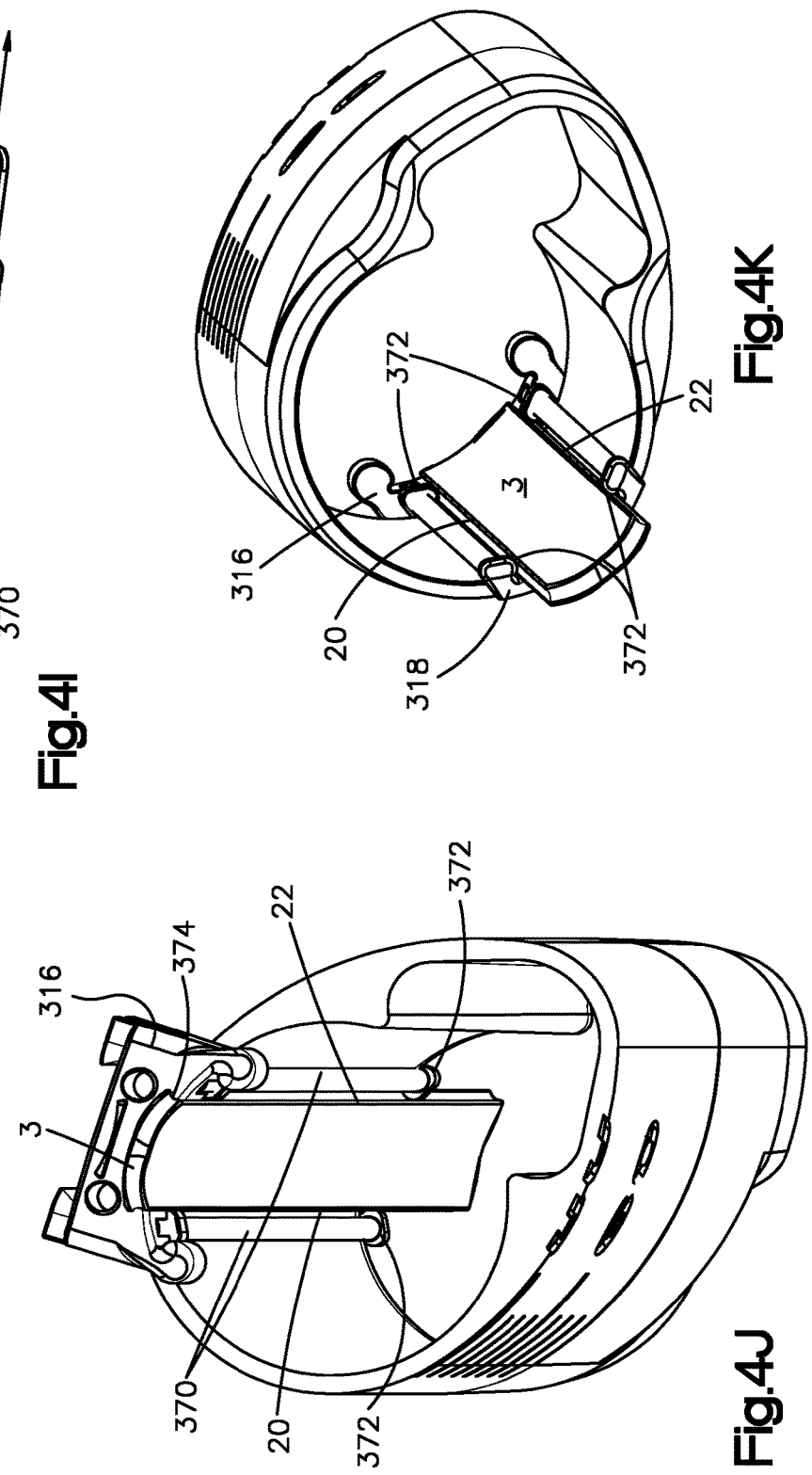

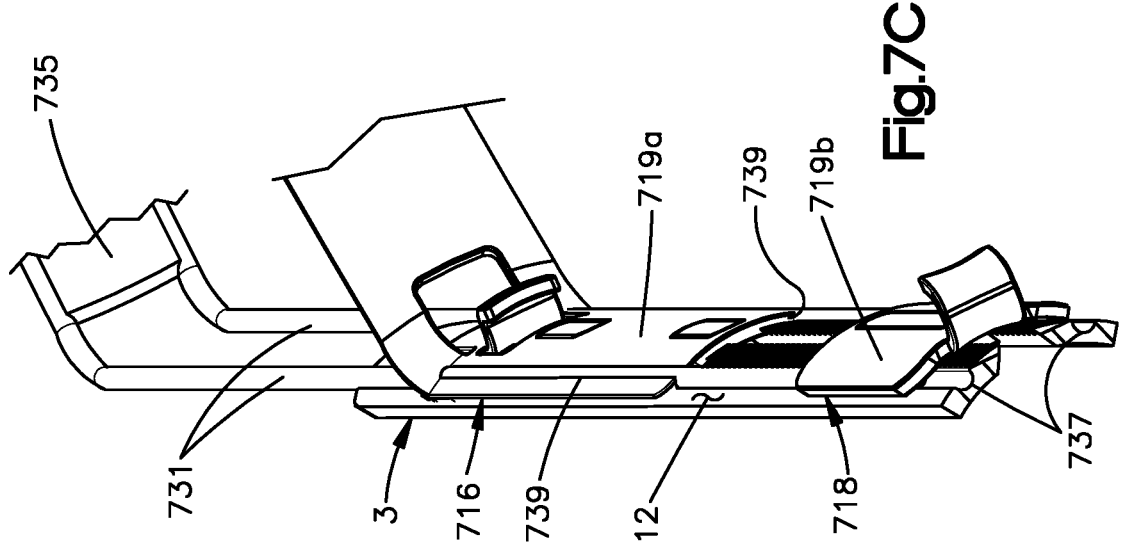
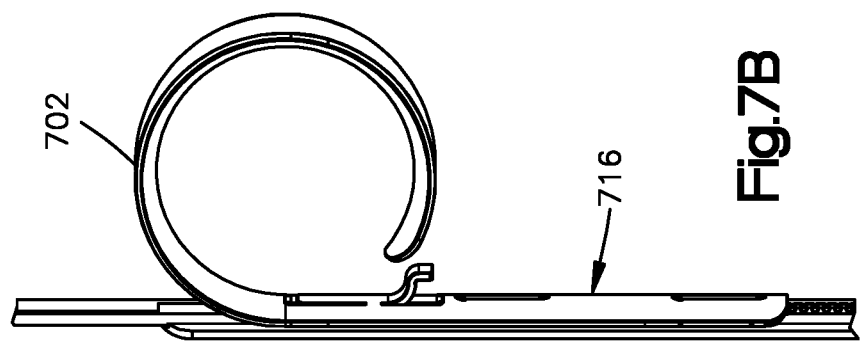
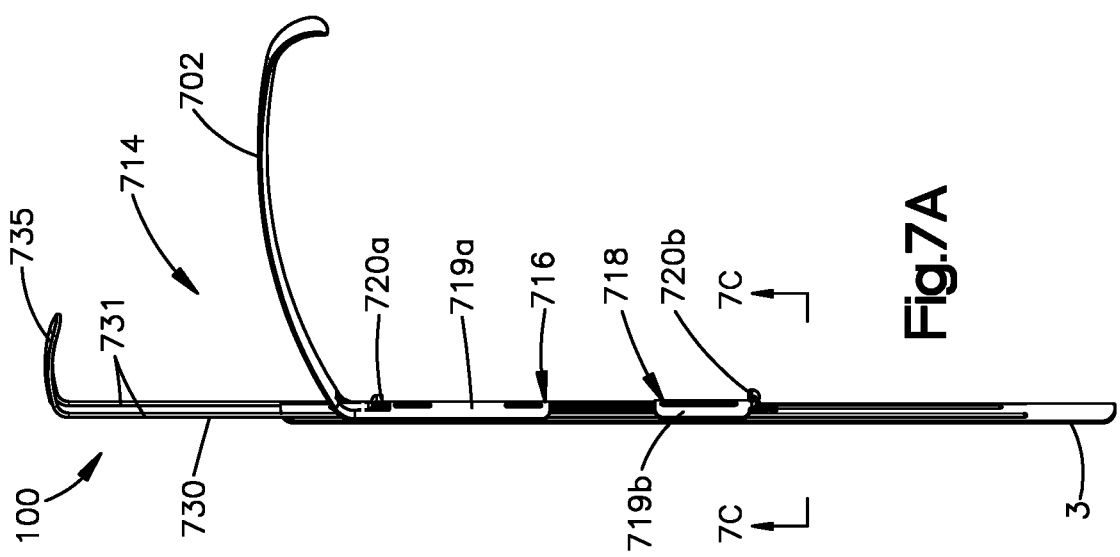

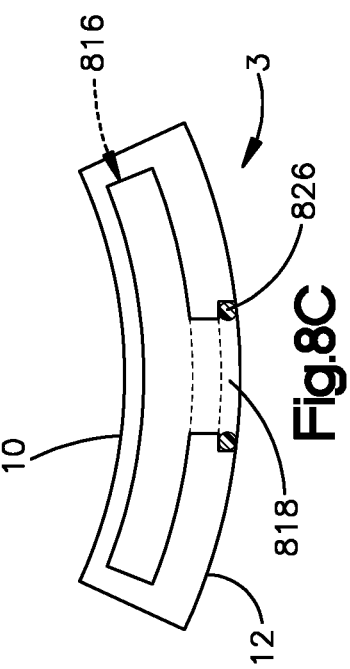
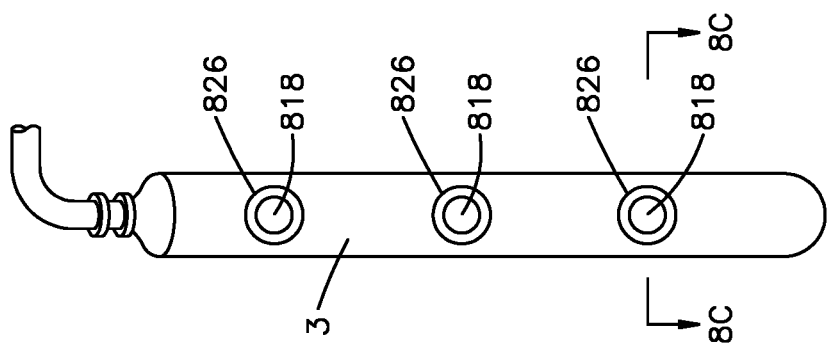
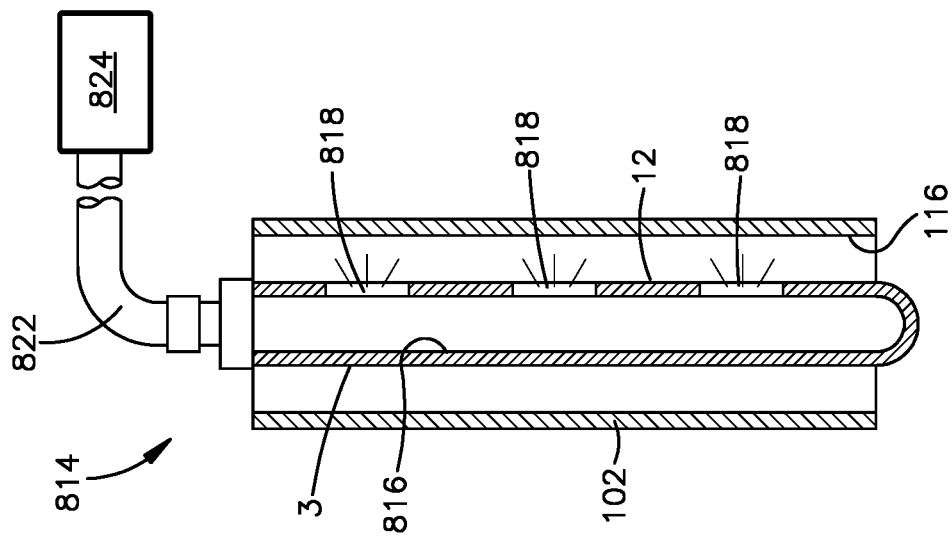

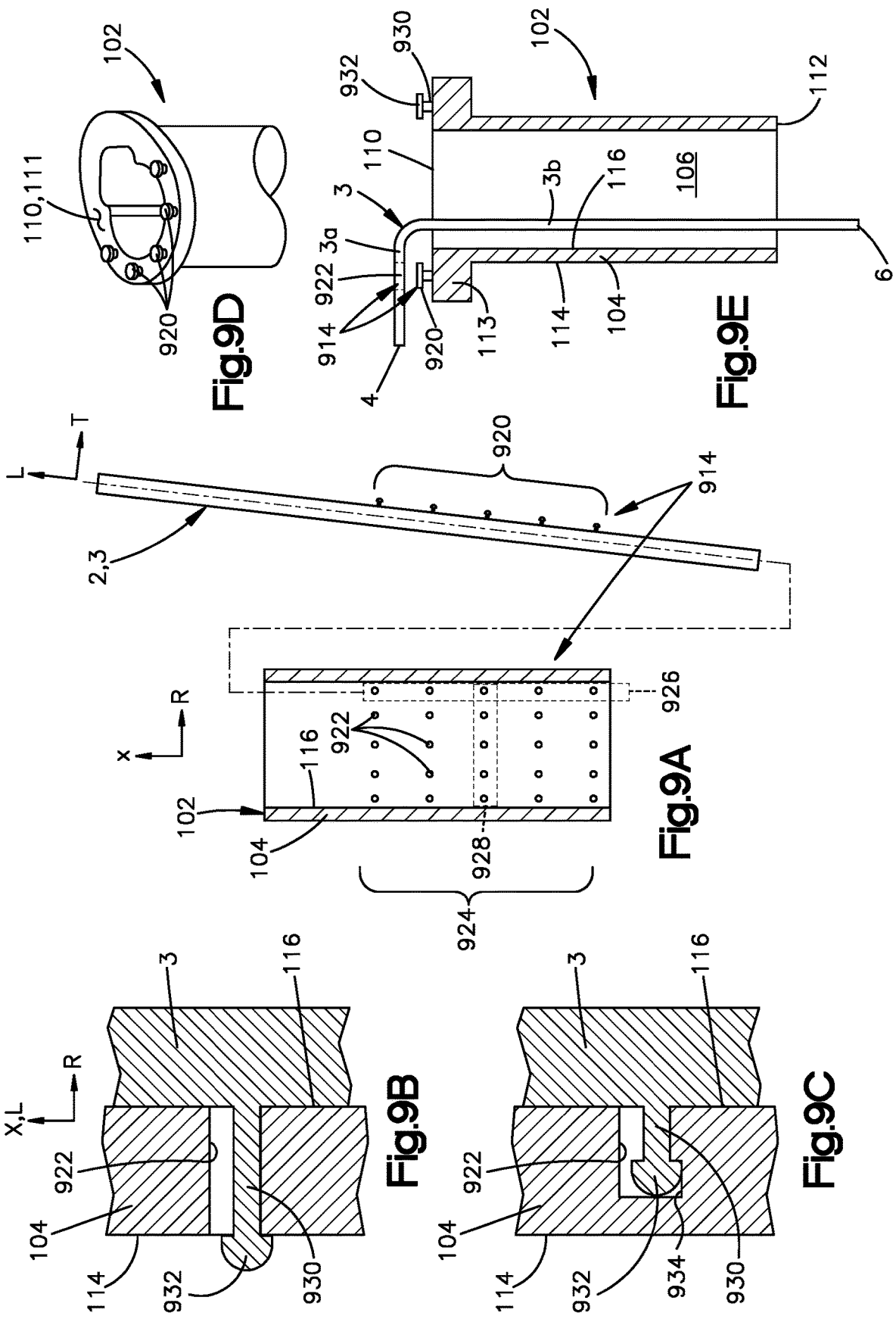

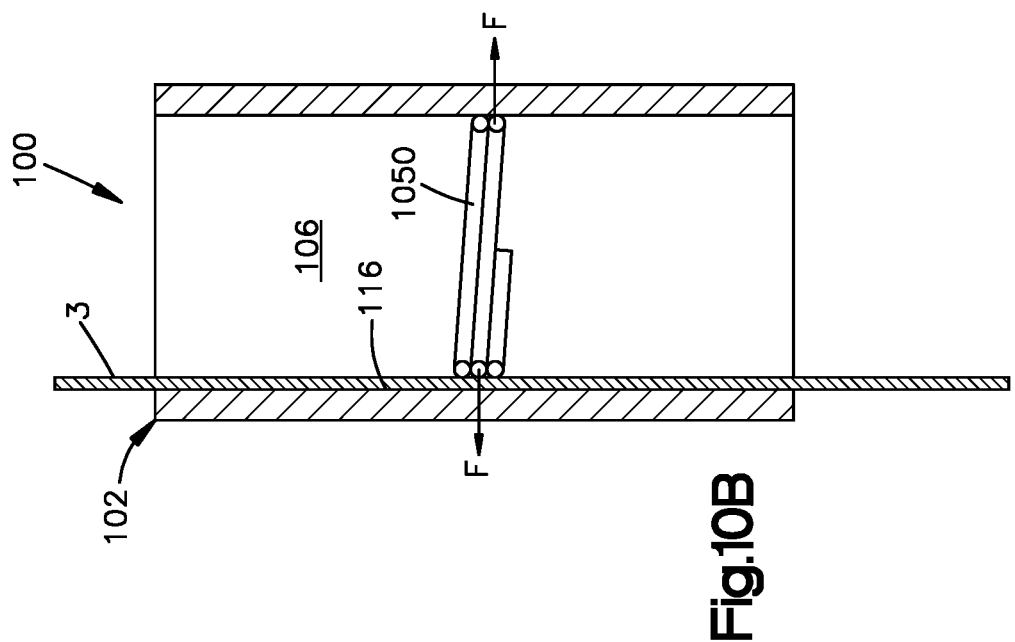
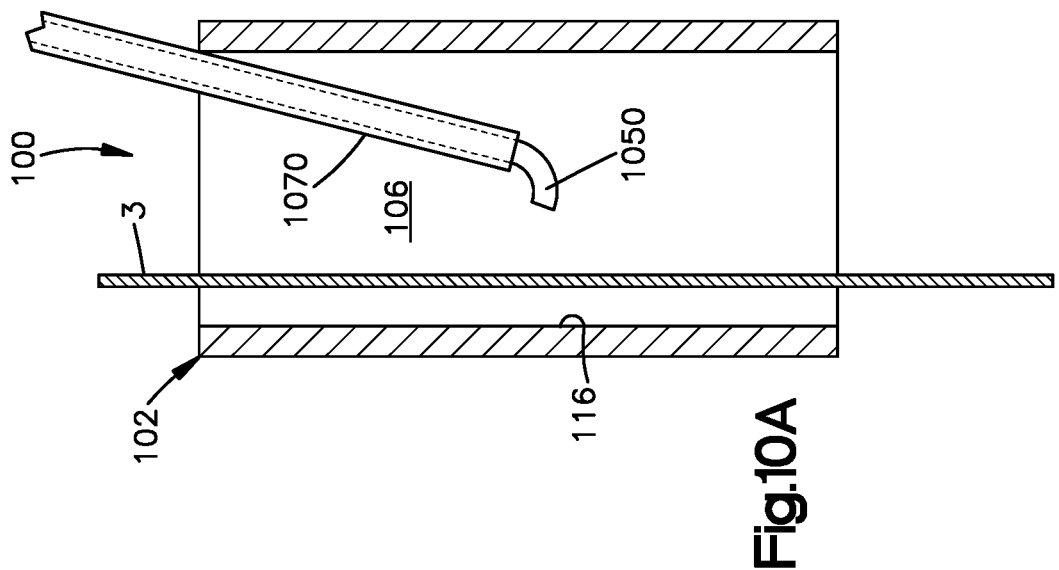

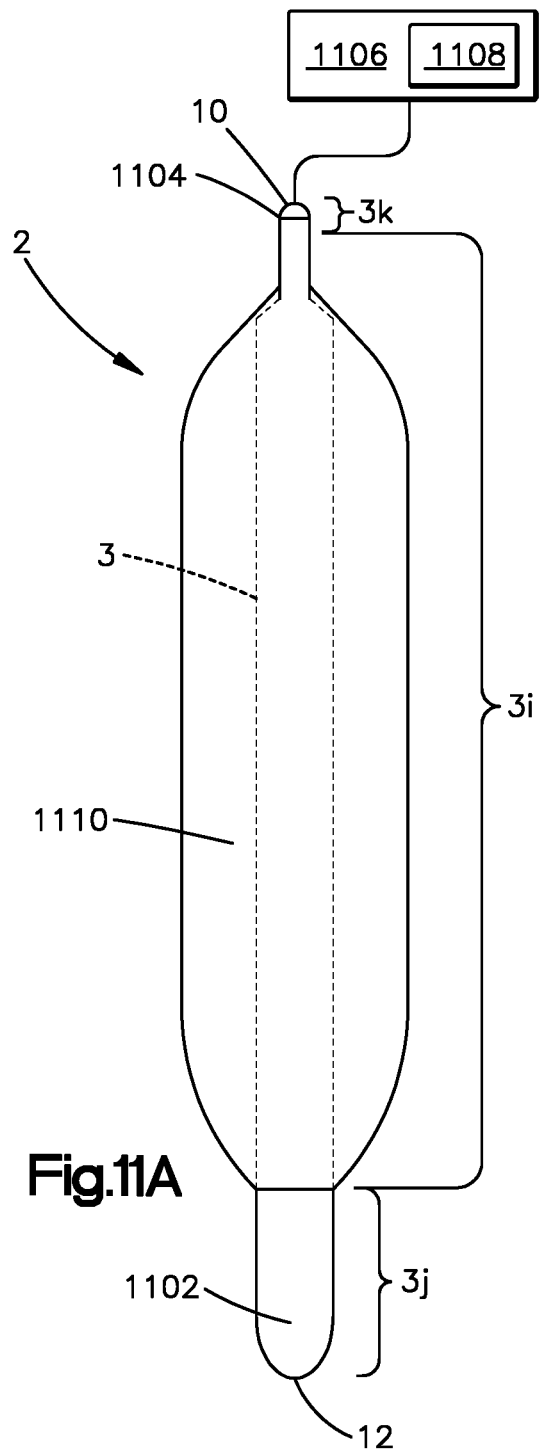
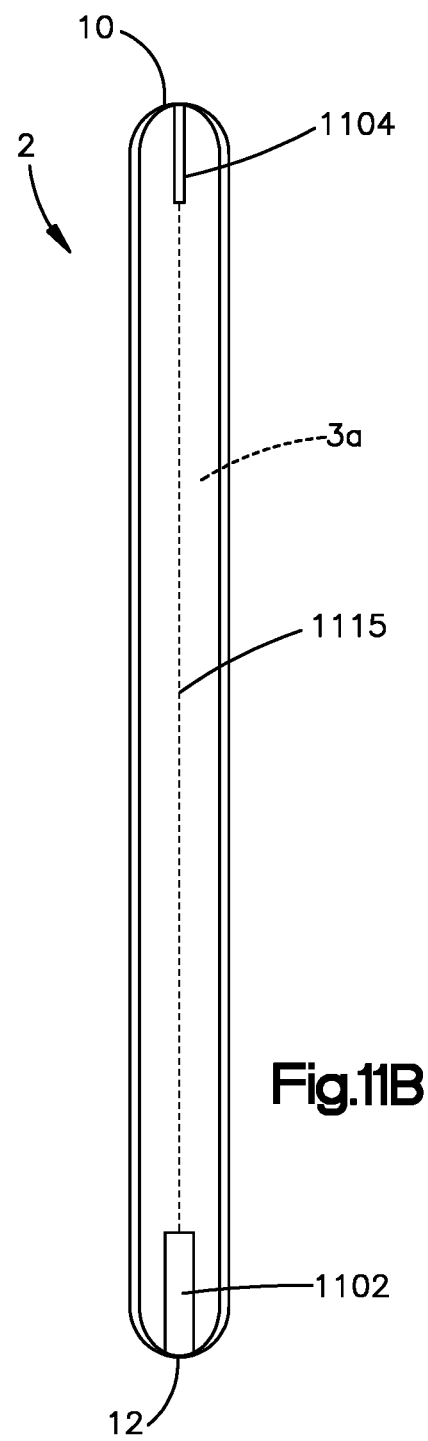

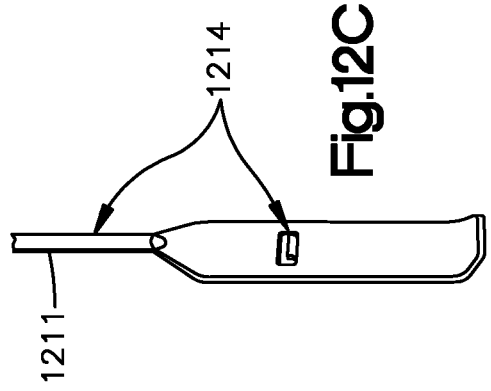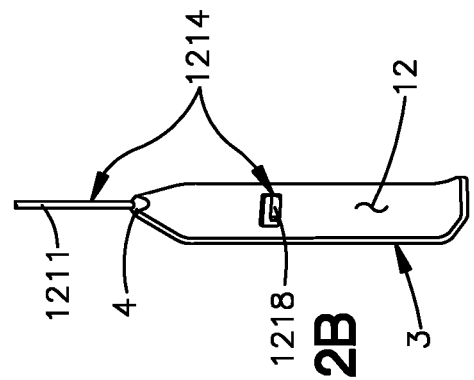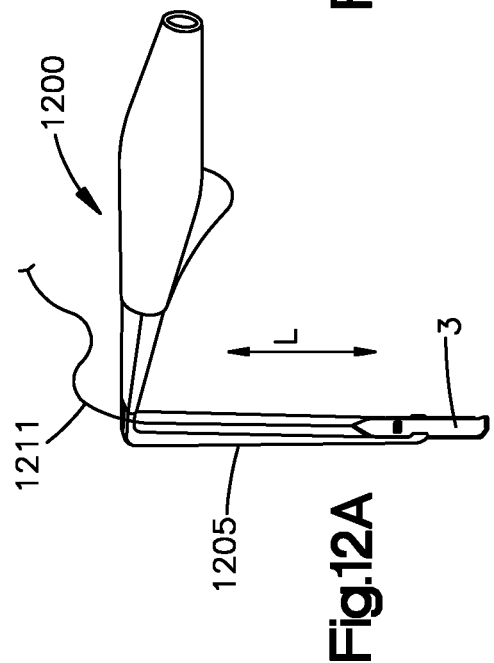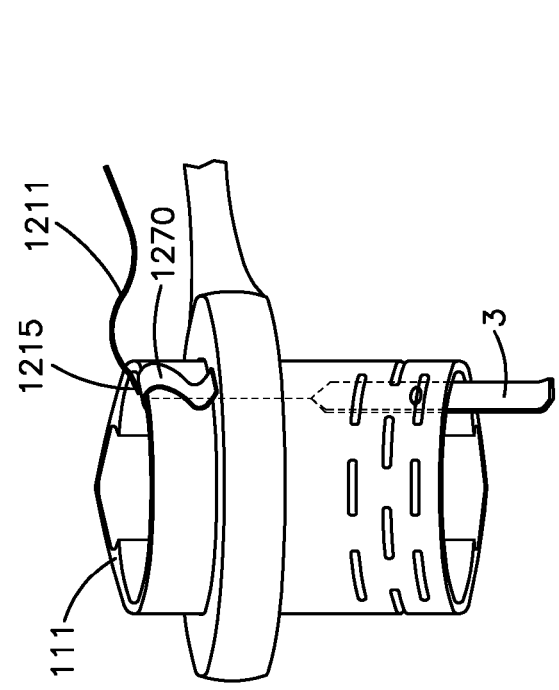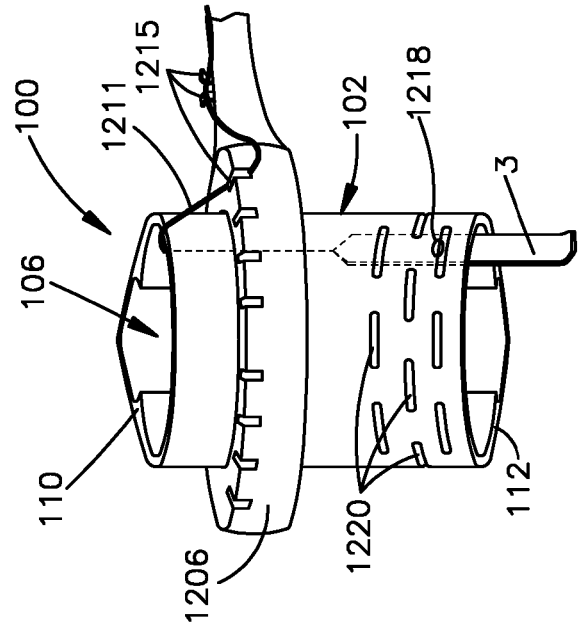

RETRACTOR MEMBERS, AND RELATED SYSTEMS AND METHODS

TECHNICAL FIELD

The present invention relates to retractor members for retracting soft tissue at a surgical treatment site within patient anatomy, as well as to systems and methods related to positioning the retractor members relative to an access tube.

BACKGROUND

Access tubes and/or retractors can be used to provide a physician with an access portal or "working channel" to a surgical treatment site within patient anatomy. Various minimally invasive procedures, including spinal procedures such as decompression, fusion, external fixation, and the like, may be performed through such access portals. The access tubes used in these procedures must often be secured in position relative to the treatment site via external devices, such as operating table-mounted devices and/or anatomical-mounted devices, such as bone anchors, including pedicle anchors and the like, by way of non-limiting examples. Once the access tube is positioned relative to the patient anatomy so as to provide the working channel open to the target treatment site, retractor members (also referred to as "retractor blades" or simply "blades"), can be inserted through the working channel and manipulated to engage soft tissue at the treatment site and pull the soft tissue toward the wall of the access tube. Additional retractor members can be inserted through the working channel as needed to pull additional soft tissue at the treatment site toward the wall of the access tube. In this manner, soft tissue can be retracted from the treatment site, providing the physician with increased access to and visualization of the treatment site, including visualization of the exiting nerve. However, during a surgical procedure, some of the soft tissue can tend to move or "creep" into the distal opening of the access tube, which can impede visualization of the treatment site, including visualization of the exiting nerve.

SUMMARY

According to an embodiment of the present disclosure, a retractor member that is configured for insertion through a channel of an access member and for moving soft tissue at a treatment site accessible through the channel includes a body having a proximal end and a distal end and spaced from each other along a longitudinal direction. The distal end defines a retractor blade and the body defines a first surface and a second surface opposite each other along a transverse direction substantially perpendicular to the longitudinal direction. The retractor includes an attachment device configured to selectively attach the body to a portion of the access member such that the body is extendable through the working channel and is translatable relative to the access member along the longitudinal direction while the body is attached to the portion of the access member.

According to another embodiment of the present disclosure, a system for retracting soft tissue includes an access member having a proximal end and a wall that extends from the proximal end to a distal end of the access member. The wall extends about a central axis in a plane orthogonal to the central axis such that an inner surface of the wall defines a channel that extends along an axial direction oriented along the central axis. The system includes a retractor body having a proximal end and a distal end that is configured to engage soft tissue and is spaced from the proximal end of the retractor body along a longitudinal direction. The retractor body defines a first surface and a second surface opposite each other along a transverse direction substantially perpendicular to the longitudinal direction. The system includes an attachment device that is coupled to the retractor body and includes a proximal mount and a distal mount configured to respectively mount to the proximal and distal ends of the access member. At least one of the proximal and distal mounts is configured to move between an unlocked configuration, in which the proximal and distal mounts are longitudinally spaced from each other by a first distance, and a locked configuration, in which the proximal and distal mounts are longitudinally spaced from each other by a second distance less than the first distance. The second distance corresponds to a distance between the proximal and distal ends of the access member along the axial direction.

According to an additional embodiment of the present disclosure, a system for retracting soft tissue includes an access member having a proximal end and a wall that extends from the proximal end to a distal end of the access member. The wall extends about a central axis in a plane orthogonal to the central axis such that an inner surface of the wall defines a channel that extends along an axial direction oriented along the central axis. The system includes a retractor body having a proximal end and a distal end that is configured to engage soft tissue and is spaced from the proximal end of the retractor body along a longitudinal direction. The retractor body defines a first surface and a second surface opposite each other along a transverse direction substantially perpendicular to the longitudinal direction. At least one of the access member and the retractor body defines one or more openings, while the other of the access member and the retractor body includes one or more protrusions that are complimentary with the one or more openings and are configured for insertion within the one or more openings so as to couple the retractor body to the access member.

BRIEF DESCRIPTION OF THE DRAWINGS

The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings:

FIG. 1B is another perspective view of the spinal surgical system illustrated in FIG. 1A, showing working channel of a tubular access member of the surgical access system;

FIG. 1C is a perspective view of the surgical access system illustrated in FIG. 1B, showing a retractor disposed within the working channel of the access member, in which a proximal portion of the retractor is bent relative to a distal portion of the retractor and away from the working channel, according to an embodiment of the present disclosure;

FIG. 1D is a partial top view of the access member illustrated in FIG. 1C having a retractor affixed to an inner wall surface of the access member;

FIG. 2A is a perspective view of a retractor that includes has straight ends and includes a flexible attachment spring for securing the retractor to the inner wall surface of the access member illustrated in FIGS. 1A-1C, according to an embodiment of the present disclosure;

FIG. 2B is a perspective view of a retractor having angularly offset ends and being otherwise similar to the retractor illustrated in FIG. 2A, according to an embodiment of the present disclosure;

FIG. 2C is a partial side view of the retractor illustrated in FIG. 2B;

FIG. 2D is a perspective view of a retractor having flared ends and being otherwise similar to the retractor illustrated in FIG. 2A, according to an embodiment of the present disclosure;

FIG. 2E is a perspective view of a retractor having flared and angular offset ends and being otherwise similar to the retractor illustrated in FIG. 2A, according to an embodiment of the present disclosure;

FIG. 3D is a partial sectional perspective view of a surgical access system having an access member, a retractor, and a separate attachment spring having carrying one or more magnets for magnetic attachment to the retractor, according to an embodiment of the present disclosure;

FIG. 4A is a perspective view of a surgical access system including an instrument in a coupled configuration with an attachment device of a retractor, in which configuration the instrument can manipulate the retractor for engaging and retracting soft tissue accessible through the working channel, further illustrating the attachment device in a locked configuration with the access member, the attachment device being operable by the instrument for attaching the retractor to a select circumferential location of the access member, the attachment device being further configured to allow longitudinal translation of the retractor relative to the access member while the attachment device is in the locked configuration, according to an embodiment of the present disclosure;

FIG. 4B is another perspective view of the surgical access system illustrated in FIG. 4A in the coupled and locked configurations;

FIG. 4F is a sectional perspective view of a bias mechanism of the attachment device illustrated in FIG. 4A;

FIG. 4I is a sectional perspective view of the attachment device de-coupled from the instrument illustrated in FIG. 4A, showing the retractor being longitudinally translatable relative to the attachment device and the access member;

FIG. 4J is a perspective view of the attachment device illustrated in FIG. 4I, showing guide features for guiding the translation of the retractor relative to the access member;

FIG. 4K is another perspective view of the guide features illustrated in FIG. 4J;

Figure 7D:
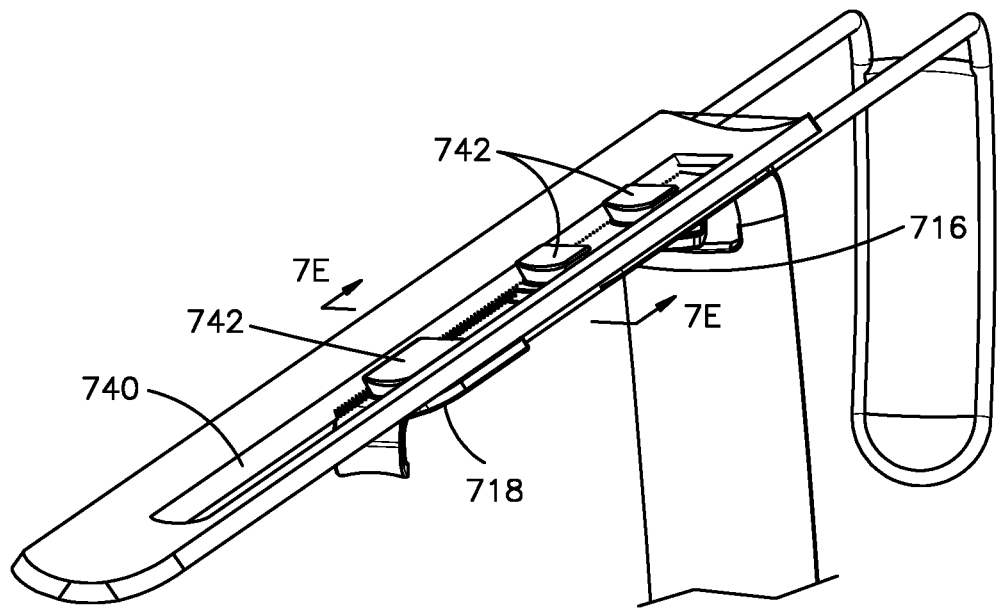
FIG. 7D is a perspective view of retractor and attachment device illustrated in FIG. 7A.
Figure 7E:
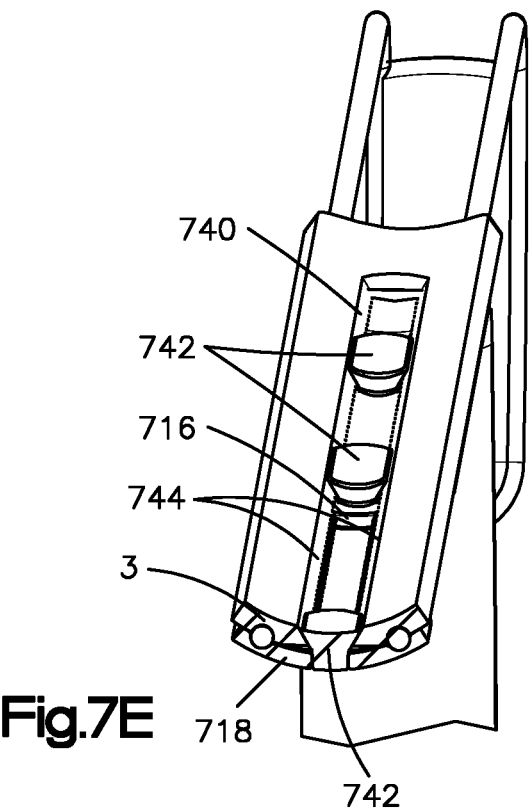
FIG. 7E is a sectional perspective view of the retractor and attachment device taken along section line 7E-7E illustrated in FIG. 7D.
Figure 7F:
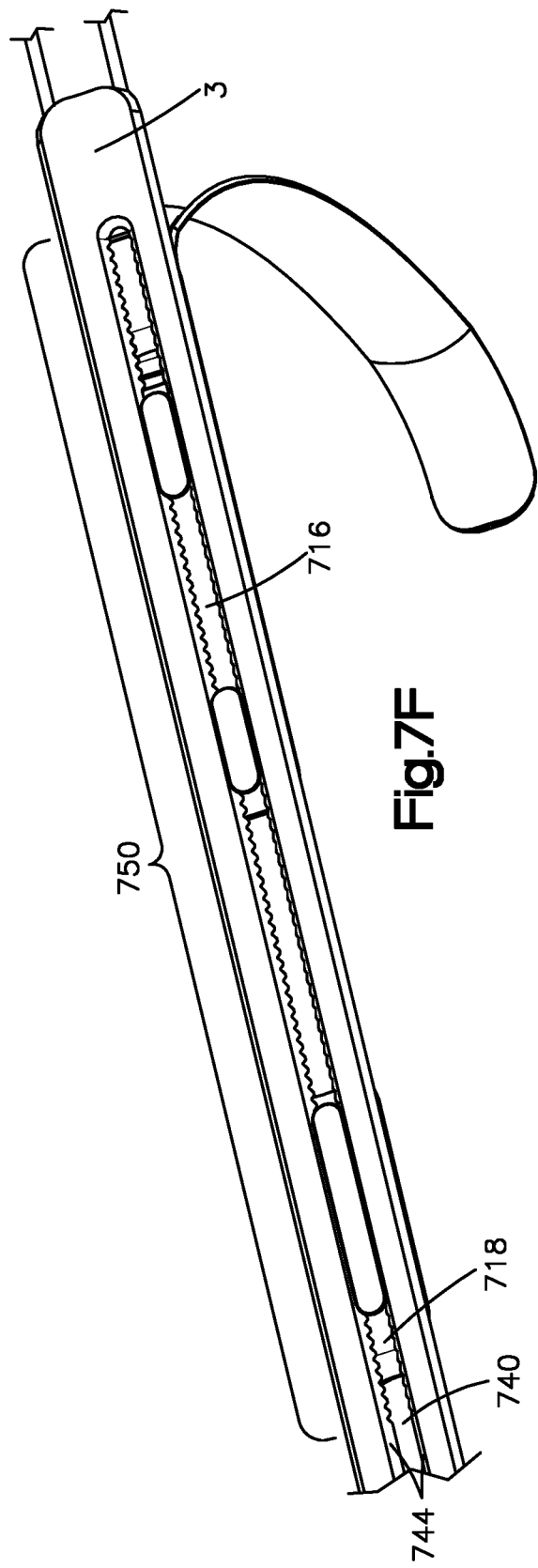
FIG. 7F is a perspective view of the ratchet mechanism illustrated in FIG. 7A.
Figure 7H:
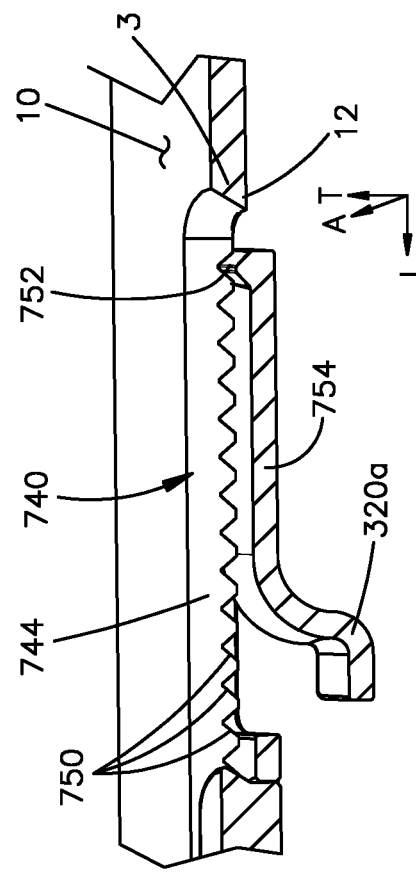
FIG. 7A is a perspective view of a retractor having an attachment device having a handle member and employing a ratchet mechanism, according to an embodiment of the present disclosure.
FIG. 7B is a perspective view of another embodiment of the handle member illustrated in FIG. 7A.
FIG. 7C is a sectional perspective view of the attachment device taken along section line 7C-7C illustrated in FIG. 7A.
FIG. 7G is a rear plan view of a pawl of the ratchet mechanism illustrated in FIG. 7A, with the handle member sectioned for visibility purposes.
Figure 7G:
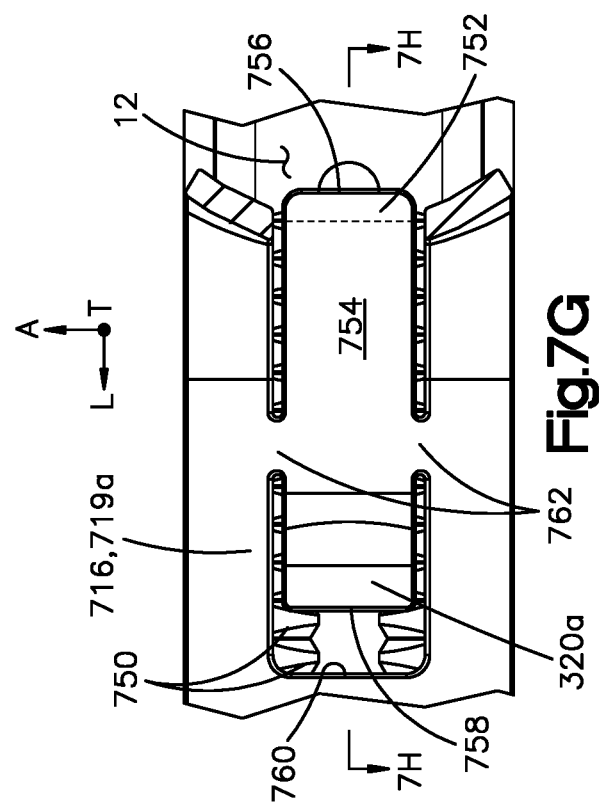
Figure 10D:
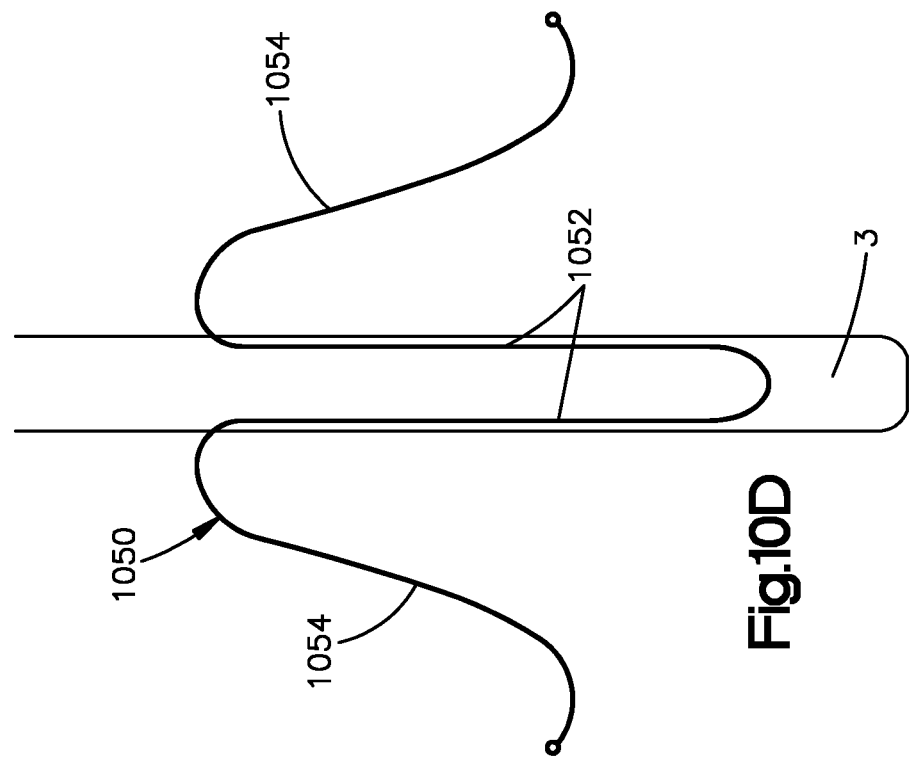
Figure 10C:
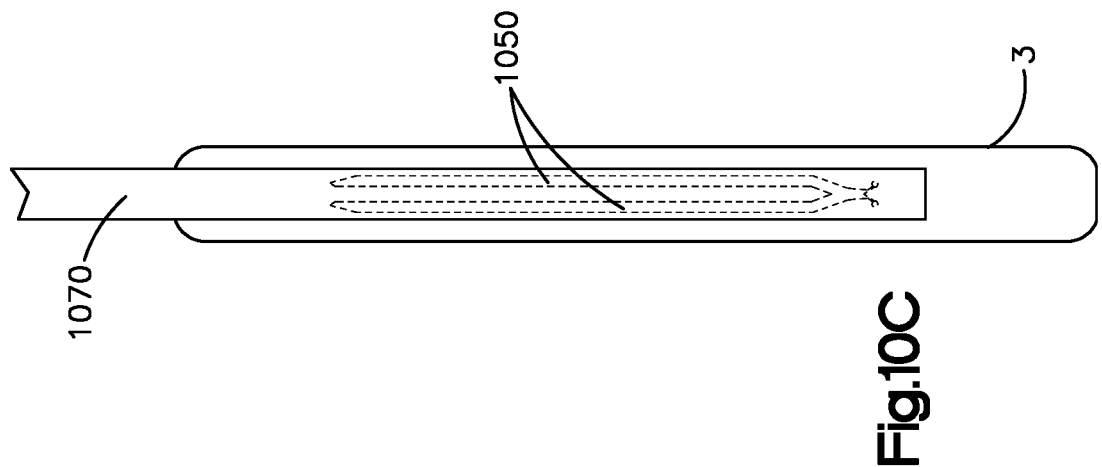

7H is a sectional perspective view of the pawl taken along section line 7H-7H illustrated in FIG. 7G;

FIG. 8A is a sectional view of a retractor having a suction attachment device for attaching the retractor to a select circumferential location of the access member, according to an embodiment of the present disclosure;

FIG. 8B is a rear plan view of the retractor illustrated in FIG. 8A;

FIG. 8C is a sectional end view of the retractor taken along section line 8C-8C illustrated in FIG. 8B;

FIG. 9A is an exploded, partial sectional view of a surgical access system having an attachment device that includes protrusions and complimentary openings configured for selective mating engagement to attach the retractor to a select circumferential location of the access member, according to an embodiment of the present disclosure;

FIG. 9B is a sectional side view showing mating engagement between a protrusion and opening illustrated in FIG. 9A;

FIG. 9C is a sectional side view showing an alternative mating engagement between a protrusion and opening illustrated in FIG. 9A;

FIG. 9D is a perspective view of an access member having a proximal surface and a series of protrusions arranged circumferentially along the proximal surface for selective mating engagement with a complimentary opening in a retractor;

FIG. 9E is a sectional side view of a retractor near mating engagement with the access member illustrated in FIG. 9D;

FIG. 10A is a partial sectional view of a surgical access system that includes an introducer for inserting a flexible wire attachment device, shown in an insertion configuration, into the working channel of an access member, according to an embodiment of the present disclosure;

FIG. 10B is a sectional view of the surgical access system illustrated in FIG. 10A, showing the flexible wire attachment device in a deployed configuration in which the flexible wire attachment device secures the retractor to an inner wall surface of the access member;

FIG. 10C is a front view of another embodiment of a flexible wire attachment device loaded in an introducer in an insertion configuration;

FIG. 10D is a front plan view of the flexible wire attachment device illustrated in FIG. 10C, shown in a deployed configuration;

FIG. 11A is a front plan view of a retractor having an electrically insulative sheath and also having a sensor for obtaining electrical information at a surgical treatment site;

FIG. 11B is a front plan view of a retractor constructed of an electrically insulative material and having a sensor for obtaining electrical information at a surgical treatment site;

FIG. 12A is perspective view of an instrument carrying a retractor that includes a tether, according to another embodiment of the present disclosure;

FIG. 12B is a perspective view of the retractor illustrated in FIG. 12A;

FIG. 12C is a perspective view of the retractor having an alternative tether, according to another embodiment of the present disclosure;

FIG. 12D is a perspective view of a surgical access system employing the retractor shown in FIG. 12A, the surgical access system having receiving formations for connection to the tether, according to an embodiment of the present disclosure; and FIG. 12E is a perspective view of the surgical access system shown in FIG. 12D having a retention clip for connection to the tether, according to another embodiment of the present disclosure.

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

The embodiments described below pertain to retractor members (also referred to herein as "retractors") for use in a surgical access system that includes an access member, such as an access tube. In particular, the embodiments described below pertain to retractors configured for insertion through a working channel of the access member to engage and retract soft tissue at a surgical treatment site distally located from the working channel. More particularly, the embodiments described below include various attachment devices allowing selective attachment of the retractor to a circumferential location of the access tube, thereby securing the soft tissue in a retracted position. As used herein with reference to an access member, the term "circumferential" generally refers to a direction revolving around a central axis of the access member, and specifically refers to any direction having a directional component that is offset from both (1) a radial direction perpendicular to the central axis and (2) an axial direction along which the central axis extends. Thus, the term "circumferential," as used herein with reference to an access member, refers to a direction along any of a line, an arc, a circle, an ellipse, a polygon, or an irregular shape, that revolves at least partially around the central axis of the access member.

Some of the attachment devices described below are located entirely on the retractor, while others are employed in complimentary components or features of the retractor and the access member, while yet others are employed is a separate component of the surgical access system. Additionally, a majority of the attachment devices described below allow the retractor to move in the following ways relative to the access member, while yet remaining secured to an inner wall surface thereof: translation along an axial direction oriented along a central axis of the member; and rotation (i.e., revolution) about the central axis circumferentially along the inner wall surface. These movements allow the physician to adjust the retractor position within the working channel as needed to account for variations in patient anatomy (e.g., variations between the anatomies of different patients). Such retractors and complimentary attachment devices that are moveable in any of the foregoing ways can also be repositioned during a surgical procedure to adjust the retraction of soft tissue as needed, while yet remaining attached to the inner wall surface so that when the physician has repositioned the retractor to satisfaction, the attachment device will hold the position of the retractor relative to the access member after the physician releases the retractor.

In additional embodiments described below, the retractor is employed as part of a surgical access system that includes an instrument coupled to a proximal end of the retractor and configured for manipulating the retractor to engage soft tissue. The instruments described below are configured to selectively couple with and de-couple from the retractor as needed. In further embodiments, the insertion instrument is also configured to actuate the attachment device from an un-attached configuration, in which the attachment device is un-attached to the access member, to an attached configuration, in which the attachment device attaches the retractor to the access member, as described above.

Figure 1A:
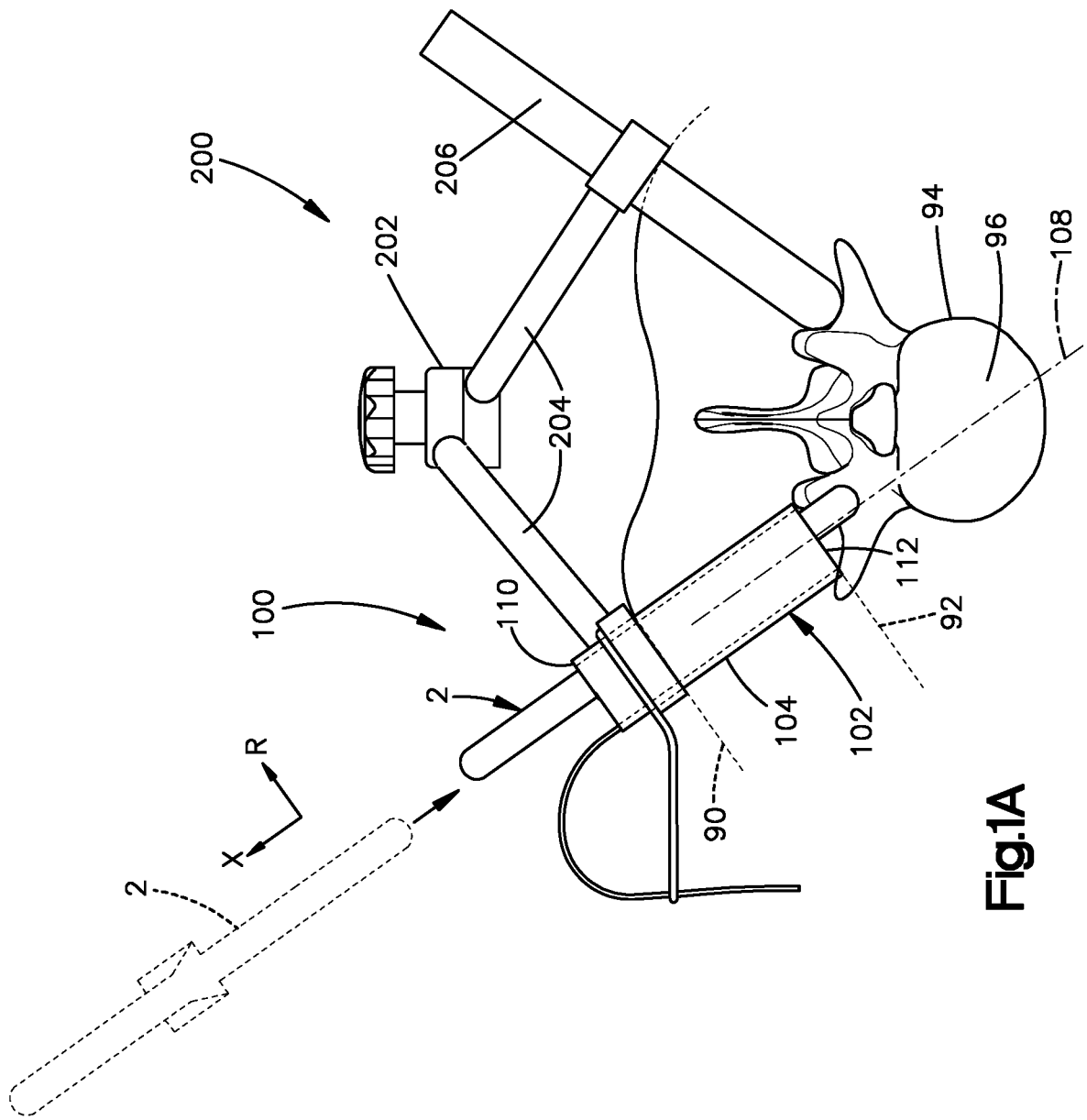
FIG. 1A is a perspective view of a spinal surgical system that includes a surgical access system, according to an embodiment of the present disclosure.

Referring now to FIG. 1A, an exemplary embodiment of a surgical access system 100 for a spinal procedure includes an access member 102 for providing access to a surgical treatment site within the patient and a retractor member 2 configured to extend through the access member 102 and engage soft tissue at the treatment site. The access member 102 has a body 103, which can be tubular, and is configured to extend distally from an ex vivo location with respect to patient anatomy to an in vivo target location within the patient anatomy. By way of a non-limiting example, the access member 102 can be configured to extend through the skin line 90 and to the target location, which is at or adjacent an intended surgical treatment site. The access member 102 includes a shield or wall 104 that defines an internal port or channel 106, also referred to herein as a "working channel" 106, that is elongate along a central axis 108 of the access member 102 and is open from the ex vivo location to the target location along an axial direction X (i.e., the direction oriented along the central axis 108). The access member 102 extends from a proximal end 110 to a distal end 112 along the axial direction X. In the illustrated example, the central axis 108 defines a spinal approach axis, which is oriented along a transforaminal approach, such as through the Kambin's triangle. In this example, the target location of the access member 102 is at the facet line 92 of adjacent vertebral bodies 94, and the treatment site includes the intervertebral disc space 96. It should be appreciated, however, that other approaches are within the scope of the present disclosure, including but not limited to interlaminar, lateral, and anterior approaches. With the access member 102 positioned at the proper depth and orientation so as to extend to the treatment site, the central axis 108 intersects the treatment site. In this manner, instrumentation can be advanced distally through the access member 102 toward the treatment site as needed. To prepare the treatment site for certain instruments, one or more retractor members 2 can be inserted through the working channel 106, such as along the central axis 108, and can be manipulated to engage and retract soft tissue (including soft tissue near the exiting nerve), such as by pulling or otherwise moving the soft tissue along a radial direction R away from and substantially perpendicular to the central axis 108 (and thus also substantially perpendicular to the axial direction X). If a portion of the engaged soft tissue extends within the working channel, the retraction moves such soft tissue toward the wall 104 of the access member 102. The retraction of soft tissue can be employed, among other things, to expose and provide visualization of the exiting nerve so that the physician can avoid damaging or contacting the exiting nerve during the spinal procedure.

The surgical access system 100 can be employed as a sub-system of a primary surgery system 200, such as a spinal surgery system. With respect to the spinal surgical procedure depicted, the spinal surgery system 200 can include, among other things, a connector 202 having one or more arms 204 for connecting the access member 102 to an anchor, such as a pedicle anchor, such as a contra-lateral pedicle anchor 206, as shown. In this manner, the position of the access member 102 and its working channel 106 can be affixed relative to the patient anatomy, such as via the anchor 206 and the connector 202. The spinal surgery system 200 can be configured as more fully described in U.S. Patent Publication No. 2018/0008253 A1, published Jan. 11, 2018, entitled "MULTI-SHIELD SPINAL ACCESS SYSTEM" ("the '253 Reference"); and U.S. patent application Ser. No. 16/692,342, filed Nov. 22, 2019, entitled "CONTROL MEMBER FOR ADJUSTING ACCESS TUBE POSITION, AND RELATED SYSTEMS AND METHODS" ("the '342 Reference"), the entire disclosure of each of which is incorporated by reference herein.

Referring now to FIGS. 1B through 1D, the wall 104 of the access member 102 defines an outer wall surface 114 and an inner wall surface 116 spaced from each other along the radial direction R. As shown, the outer wall surface 114 can have an oblong profile in a plane orthogonal to the central axis 108. Additionally, the wall 104 can also define a secondary channel 107 along the axial direction X. For example, the inner wall surface 116 can define one or more projections 117 that extend generally radially inward toward the central axis 108 so as to define a partition between the working channel 106 and the secondary channel 107. In the illustrated embodiment, the secondary channel 107 can receive one or more optical instruments, such as a camera or other type of image sensor, by way of non-limiting examples. In such embodiments, the partition between the working channel 107 and the secondary channel 107 is helpful for preventing mechanical interference between the optical instrument(s) and any instruments extending through the working channel 106. The secondary channel 107 is preferably open to the working channel 106 at least along a direction having a directional component along the radial direction R. As shown, the wall 104 can extend an entire revolution about the central axis 108, thereby providing the access member 102 with its tubular configuration. It should be appreciated, however, that the wall 104 can extend less than a full revolution about the central axis 108, while continuing to provide a working channel 106 and optionally also a secondary channel 107.

As shown in FIG. 1C, the retractor member 2 (also referred to herein as a "retractor" 2) has a retractor body 3 that extends from a proximal end 4 to a distal end 6 spaced from each other along a longitudinal direction L. It should be appreciated that the retractor body 3 can define the entire retractor 2 in monolithic fashion, or can define a portion of the retractor 2, such as a major portion thereof in combination with one or more separate yet connected (or connectable) portions of the retractor 2, by way of non-limiting examples. The distal end 6 can have a blade-like geometry, and can thus be referred to as a "retractor blade" or simply a "blade". The retractor 2 has a length along the longitudinal direction L greater than a length of the access member 102 along the axial direction X. In this manner, the retractor 2 can be inserted through the working channel 106 to the treatment site and can be manipulated by its proximal end 4 so as to control placement of the distal end 6 to engage soft tissue as needed at or near the treatment site. It should be appreciated that the proximal end 4 can also have a blade-like geometry and can thus also be referred to as a "retractor blade" or "blade". Such opposed-blade configurations can be advantageous because they need not require a specific end to be inserted through the access member 102.

With the soft tissue engaged, the retractor 2 can be moved to the inner wall surface 116 and attached thereto by an attachment device, described in more detail below. As shown in FIG. 1D, the retractor body 3 has a first or "inner" surface 10 and a second or "outer" surface 12 spaced from each other along a transverse direction T substantially perpendicular to the longitudinal direction L. The outer surface 12 of the retractor body 3 is preferably arcuate and convex in a plane orthogonal to the longitudinal direction L. Additionally, the outer surface 12 preferably defines a radius R1 substantially equivalent to a radius R2 of the inner wall surface 116. In this manner, the retractor body 3 can be moved flush against the inner wall surface 116 for connection thereto, so as to avoid obstructing the working channel 106. It should be appreciated that when the retractor body 3 is flush against the inner wall surface 116, the transverse direction T is substantially oriented along the radial direction R of the access member 102. The inner surface 10 of the retractor body 3 is preferably arcuate and concave in the orthogonal plane, and preferably extends in parallel or concentric fashion with the convex outer surface 12 in the orthogonal plane.

The retractor 2 is formed of a material that is biocompatible (i.e., a "biomaterial") and is sufficiently rigid so that manipulation at the proximal end 4 causes retraction of soft tissue at the distal end 6 (or vice versa if the opposite end is inserted through the working channel 106). The material also preferably provides the retractor body 3 with deformability, such as via plastic deformation, allowing a first portion 3a of the retractor body 3 to be bent relative to a second portion 3b of the retractor body, as shown in FIG. 1C. In this manner, when retractor body 3 has achieved satisfactory retraction of soft tissue (and the retractor body 3 has been secured to the access member 102 by an attachment device, as described in more detail below), the physician can bend the first portion 3a away from the central axis 108 and out of the way, thereby reducing the profile of the retractor body 3 in a proximal direction P, for example. Such retractor body materials can be metal (e.g., stainless steel, such as a 300 series and/or a 400 series stainless steel), polymeric (e.g., polyphenylsulfone (PPSU)), and/or a composite material (e.g., carbon fiber), by way of non-limiting examples.

Referring now to FIGS. 2A through 2F, different variants of the retractor body 3 are shown, each of which includes an integrated attachment device 14 for coupling the retractor body 3 to the wall 104 of the access member 102. For example, the attachment device 14 is configured to attach the retractor body 3 to a circumferential portion of the inner wall surface 116 as selected by the physician. In particular, the attachment device 14 shown in each of these variants comprises at least one compliant member 16 configured to flex from a neutral configuration when disposed outside the working channel 106 to a flexed configuration when inserted within the working channel 106. The compliant member 16 can also be referred to as a "locking spring" or "locking ring". When in the flexed configuration, the compliant member 16 imparts a return force (which can also be referred to as a "locking force") against the inner wall surface 116 sufficient to push the retractor body 3 toward the inner wall surface 116, effectively securing the retractor body 3 in place relative to the wall 104. It should be appreciated that the compliant member 16 is configured such that the locking force is sufficient to maintain retraction of soft tissue engaged by the distal end 6 of the retractor body 3, yet not so great so as to prevent the physician from further subsequently manipulating the retractor body 3 to adjust engagement with soft tissue, such as to translate the retractor body 3 along the axial direction X, rotate the retractor body 3 about the central axis 108, or any combination of the foregoing motions. Furthermore, the compliant member 16 of the present embodiments is configured to effectively automatically secure the retractor body 3 in place within the working channel 106 once the physician has finished manipulating the proximal end 4 thereof (so long as the compliant member 16 resides within the working channel 106).

Each of the retractor bodies 3 defines a first side 20 and a second side 22 spaced from each other along a lateral direction A substantially perpendicular to the longitudinal and transverse directions L, T. The compliant member 16 of the attachment device 14 can include a pair of compliant members 16 or "wings" that extend circumferentially outward from the first and second sides 20, 22 at a longitudinal portion 3c of the retractor body 3 that is intermediate the proximal and distal ends 4, 6 thereof. Thus, longitudinal portion 3c can also be referred to an "intermediate" portion 3c of the retractor body 3. The retractor body 3 also defines a proximal body portion 3d that extends from the intermediate portion 3c to the proximal end 4 along the proximal direction P, and a distal body portion 3e that extends from the intermediate body portion 3c to the distal end 6 along a distal direction D. It should be appreciated that the proximal and distal directions P, D are each monodirectional components of the longitudinal direction L, which is bi-directional. A radially outer surface of the wings 16 defines a radius R3 that is slightly larger than the radius R2 of the inner wall surface 116 when in the neutral configuration. In this manner, inserting the wings 16 within the working channel 106 causes the wings 16 to flex inwardly toward the central axis 108 (and also toward one another), thereby providing the locking force. One or both of the wings 16 can define a helical end surface 18 that is contiguous with the respective first or second side 20, 22 of the retractor body 3. In the illustrated embodiments, the helical end surface 18 defines a proximal surface of each wing 16, although the distal surface of one or both of the wings 16 can also extend helically to the respective first or second side 20, 22 in similar fashion.

As shown in FIGS. 2B and 2C, the retractor body 3 can define a proximal end portion 3f that is angularly offset from an adjacent portion 3h at an acute angle α1, as measured in a plane extending along the longitudinal and transverse directions L, T, which plane can be referred to as the "L-T plane". The adjacent portion 3h can be characterized as a portion of the body 3 that extends from the end portion 3f toward the opposite end 6 of the retractor body 3. The retractor body 3 can alternatively or additionally define a distal end portion 3g that is angularly offset from the adjacent portion 3h at an acute angle α2 in the L-T plane. In embodiments where the retractor body 3 has proximal and distal end portions 3f, 3g that are angularly offset from the adjacent portion 3h, the acute offset angles α1, α2 can be substantially equivalent, as shown, or can be different from each other.

As shown in FIG. 2D, one or both of the proximal and distal end portions 3f, 3g can be flared outwardly along the lateral direction A so as to define a maximum lateral dimension A1, A2 that is greater than a maximum lateral dimension A3 of the adjacent portion 3h. In embodiments where both of the proximal and distal end portions 3f, 3g are flared outwardly along the lateral direction A, the maximum lateral dimensions A1, A2 of the end portions 3f, 3g can be substantially equivalent, as shown, or can be different from one another.

As shown in FIG. 2E, one or both of the proximal and distal end portions 3f, 3g can be both angularly offset from the adjacent portion 3h and flared outwardly along the lateral direction A relative to the adjacent portion 3h. For example, both of the proximal and distal end portions 3f, 3g can be angularly offset from the adjacent portion 3h at the same acute angle or different acute angles and can also be flared outwardly to define the same or different maximum lateral dimension. It should be appreciated that the retractor body 3 can have proximal and distal end portions 3f, 3g that are any combination of the foregoing (i.e., straight, angled, and flared).

Figure 2F:
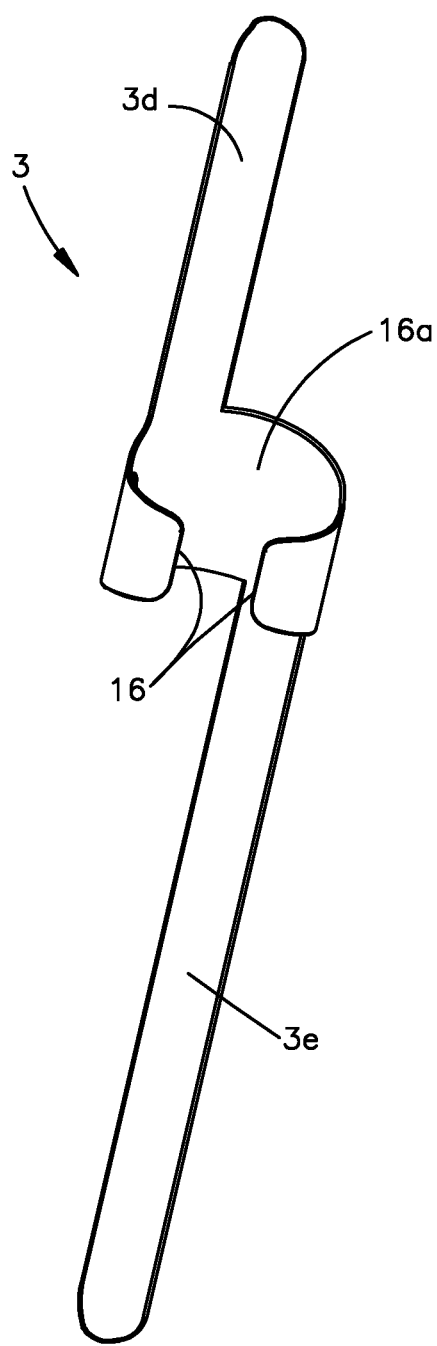
FIG. 2F is a perspective view of a retractor having flexible attaching spring and proximal and distal portions that are circumferentially offset from each other along the attachment spring.

Referring now to FIG. 2F, the proximal and distal body portions 3d, 3e can at least partially, and optionally entirely, circumferentially offset from each other. In such embodiments, the proximal body portion 3d can extend from the proximal end 4 in the distal direction D to the locking spring 16, and the distal body portion 3e can extend from the locking spring 16 in the distal direction D to the distal end 6. Additionally, in such embodiments, the locking spring 16 can include an interconnecting portion 16a that connects the proximal and distal body portions 3d, 3e together.

Figure 2G:
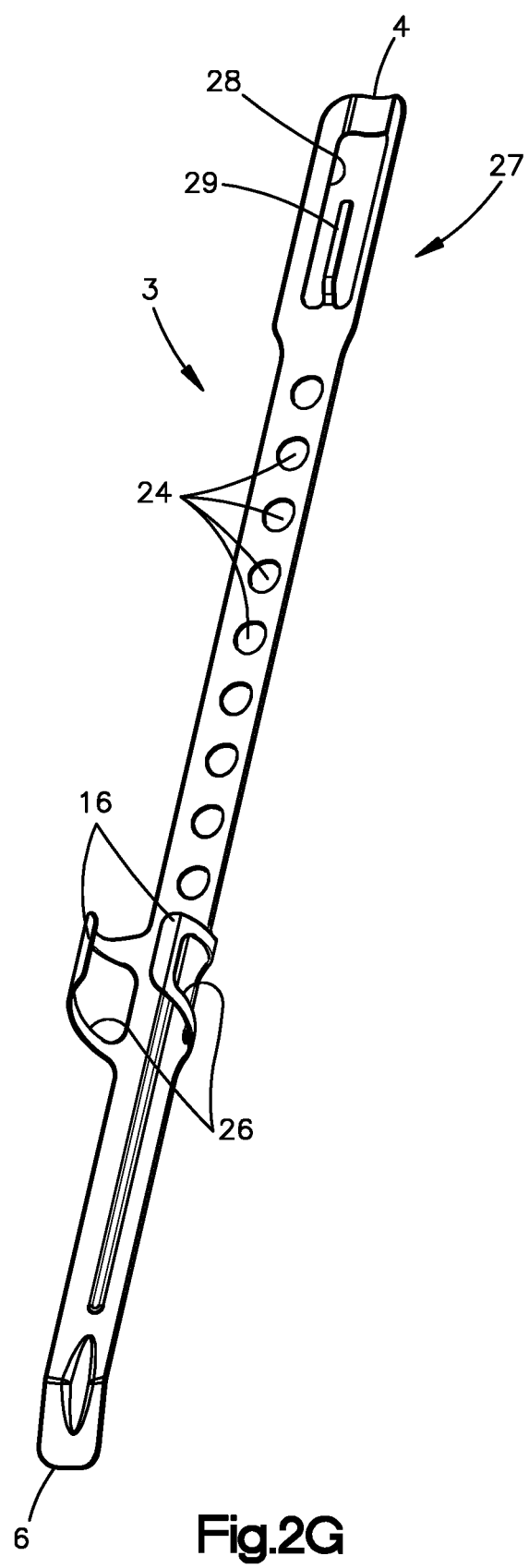
FIG. 2G is a perspective view of a retractor defining a plurality of apertures.

As shown in FIG. 2G, the retractor body 3 can include one or more features for increasing the flexibility of the respective body portions thereof. By way of non-limiting examples, the retractor body 3 can define apertures 24 extending therethrough along the transverse direction T, such as for facilitating plastic deformation in the L-T plane, such as for bending a proximal portion 3a of the body 3 out of the way once secured to the wall 104, as described above with reference to FIG. 1C. For example, the apertures 24 can effectively define bend-enhancing regions of the retractor body 3. Additionally or alternatively, one or both of the wings 16 can define an aperture 26 for increasing the flexibility of the wings 16, such as for elastically deforming between the neutral and flexed configurations described above. One advantage of employing apertures 24, 26 for increased flexibility is that stronger materials can be used to form the retractor body 3. Moreover, the apertures 26 can be elliptical in shape, which can alleviated material fatigue from multiple bends imposed at or near the same location of the retractor body 3. Additionally, at one or both of the proximal and distal ends 4, 6, the retractor body 3 can define an end formation 27 for connection to a wire, flexible tube, or other component or instrument of the surgical access system 100. A non-limiting example of such an end formation 27 can include an aperture 28 and a prong 29 extending over the aperture 27, such as along the longitudinal direction X.

It should be appreciated that the locking spring 16 of any of the foregoing embodiments can be provided at different longitudinal locations along the retractor body 3 to compensate for deflection responsive to the soft tissue engaged by the distal end 6 and/or other surrounding tissue in contact with the retractor 2. For example, any combination of the retractors 2 described above with reference to FIGS. 2A through 2G can be provided in a kit that includes multiple versions of each retractor 2, wherein the respective locking springs 16 are located at different longitudinal locations along the retractor body 3.

It should further be appreciated that the designs of the retractors 2 described above with reference to FIGS. 2A through 2G allow more than one retractor 2, such as two (2) or more retractors 2, to be inserted within the working channel 106 and secured to the inner wall surface 116 for retracting soft tissue. When a second retractor 2 is inserted into a working channel 106 that already has a first retractor 2 attached thereto, the physician can select the second retractor 2 to be one in which its locking spring 16 will be longitudinally offset from that of the first retractor 2 when both are secured within the working channel 106, thereby avoiding interference between the locking springs 16. Additionally or alternatively, the physician can select the second retractor 2 to have the same design as the first, and can elect to insert the opposite end of the second retractor 2 into the channel 106 (i.e., can flip the second retractor 2 relative to the first retractor 2) so that the locking springs 16 do not interfere with each other.

Figure 3A:
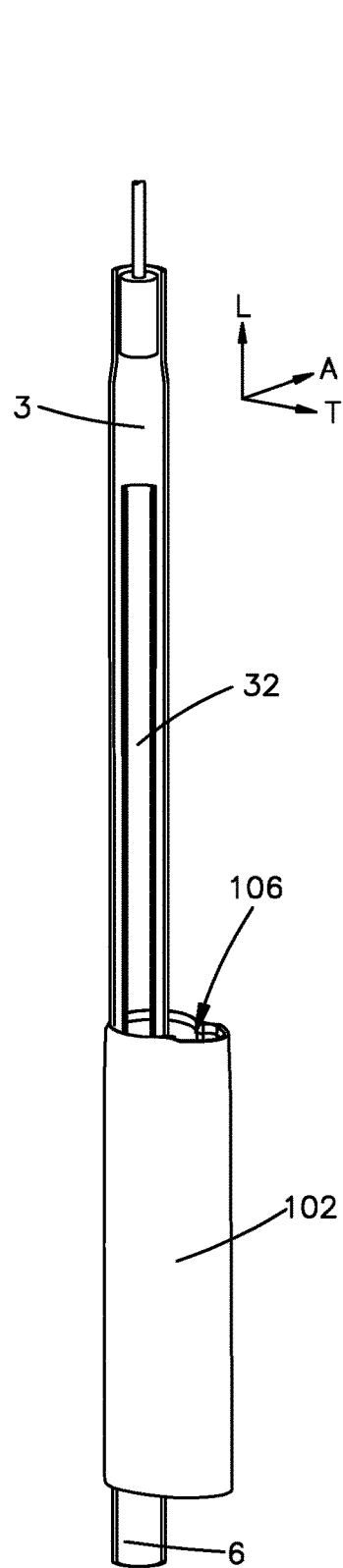
FIG. 3A is a perspective view of a surgical access system having an access member and a retractor, which has a guide feature for guiding movement of a separate attachment spring.
Figure 3B:
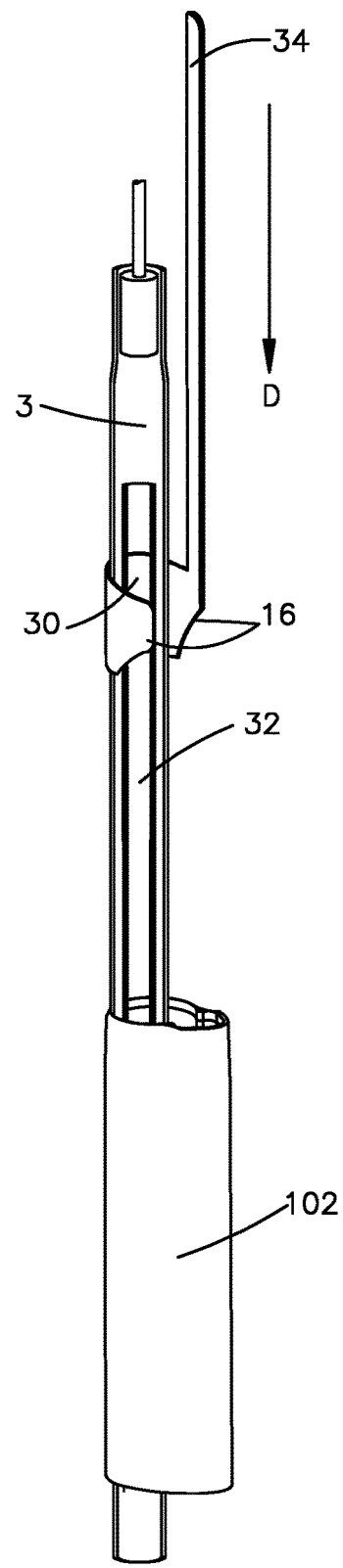
FIG. 3B is a perspective view of the surgical access system illustrated in FIG. 3A, showing the attachment spring connected to the guide feature of the retractor in a position remote from the access member.
Figure 3C:
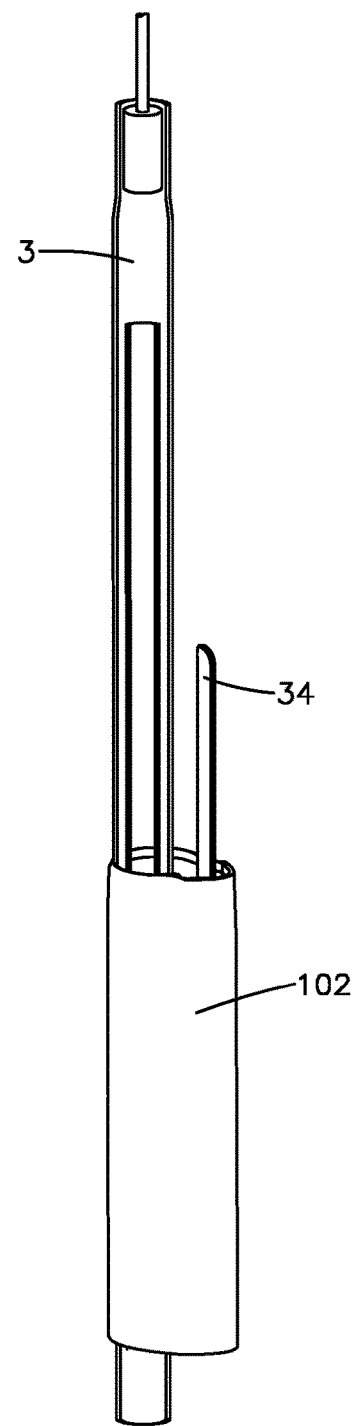
FIG. 3C is a perspective view of the surgical access system illustrated in FIG. 3B, showing the attachment spring advanced distally along the guide feature to a position within the working channel of the access member, in which the attachment spring pushes the retractor securely against the inner wall surface of the access member.

Referring now to FIGS. 3A through 3C, in other embodiments, the attachment device 14 can include an attachment member 17 that is separate from and connectable to the retractor 2, such as before, during, or after the retractor 2 is inserted through the working channel 106. In such embodiments, the retractor 2 and the attachment member 17 can have complimentary mounting formations. For example, the attachment member 17 can include a slide formation, such as a slider 30, that is configured to slidably engage a complimentary slide formation, such as a guide slot 32, of the retractor body 3. The guide slot 32 of the present embodiment guides translational, longitudinal movement of the slider 30 (and thus also the attachment member 17) along the retractor body 3 into and out of the working channel 106 as needed. The slider 30 and the guide slot 32 preferably have complimentary geometries that allow the slider 30 to enter into the guide slot 32 and vacate the guide slot 32, at least at one location of the guide slot 32, such as at a proximal end thereof. For example, a proximal end of the guide slot 32 can have a widened portion or opening that allows entry and departure of the slider 30 therein, while the reminder of the guide slot 32 is configured to retain the slider 30 therein. A distal end of the guide slot 32 can effectively provide a physical stop that prevents the slider 30 (and thus also the attachment member 17) from over-translating in the distal direction D.

Similar to the embodiments described above, the attachment member 17 includes a locking member, such as a locking spring 16, which can be configured similarly as described above. The locking spring 16 can define one or more compliant wings, each of which can be referred to as a circumferential wall that extends circumferentially away from the slide formation 30 and is configured to be flexed inwardly toward the central axis 108 of the access member 102 when the locking member 16 is disposed in the working channel 106 to supply the locking force. When inside the working channel 106, the locking spring 16 can be positioned so as to slide annularly between the outer surface 12 of the retractor body 3 and the inner surface 116 of the access member 102. The slider 30 can extend inwardly along the transverse direction T (i.e., toward the central axis 108 of the access member 102) from the locking spring 16 and into the guide slot 32. In other embodiments, the slider 30 can extend transversely outwardly from the locking spring 16, in which embodiments the retractor body 3 can be positioned annularly between the locking spring 16 and the inner wall surface 116. The attachment member 17 includes a grip member, such as a proximal extension 34, allowing the physician to manipulate the attachment member 17 along the longitudinal direction L relative to the retractor body 3. It should be appreciated that the proximal extension 34 can be configured to be bent away from the central axis 108 and out of the way so as to reduce its profile in the proximal direction P, similar to the manner described above with reference to FIG. 1C.

The retractor body 3 of the present embodiment can be freely inserted through the working channel 106 to engage soft tissue, and once so engaged, can then receive the attachment member 17, which can be advanced along the guide slot 32 along the distal direction D until the locking spring 16 resides at a desired longitudinal location within the working channel 106, at which position it provides the locking force. The longitudinal position of the attachment member 17 can thereafter be adjusted as needed, such as to reduce deflection of the retractor responsive to surrounding tissue. Furthermore, if a subsequent adjustment to the engagement between the distal end 6 of the retractor body 3 and the soft tissue is desired, the attachment member 17 can be withdrawn proximally from the working channel 106 while optionally remaining engaged with the guide slot 32, and can be re-translated within the working channel 106 as needed, such as after the adjustment to the soft tissue is complete. In this manner, the attachment member 17 can be withdrawn from the working channel 106 during re-adjustments to the soft tissue retraction, allowing the physician greater freedom to manipulate the retractor body 3 as needed.

Referring now to FIG. 3D, in other embodiments, the separate attachment member 17 and the retractor 2 can be configured for magnetic attachment to each other within the working channel 106. For example, at least a portion of the locking spring 16 of the attachment member 17 can be constructed of a ferrous (e.g., magnetic) material, and the retractor 2 can include a series of magnets 35 for selective attachment to the attachment member 17 (or at least to the ferrous portion thereof). The attachment member 17, including the locking spring 16 and the proximal extension 34 thereof, can otherwise be configured similarly as described above with reference to FIGS. 3A through 3C. In the present embodiment, the attachment member 17 can be inserted within the working channel 106 and the retractor 2 can subsequently be inserted through the working channel 106 to engage and retract soft tissue. With soft tissue engaged, the physician can move the retractor 2 toward the inner wall surface 116 (and thus also toward the locking spring 16) and can bring a select one of the magnets 35 into magnetic engagement with the locking spring 16 (or at least with the ferrous portion thereof), thereby attaching the retractor to the inner wall surface 116. In additional embodiments, the retractor 2 can be constructed of a ferrous material and the locking spring 16 can carry one or more magnets. In further embodiments, the retractor 2 and the locking spring 16 can carry opposite polarity magnets for attachment therebetween.

Referring now to FIGS. 4A through 4D, the surgical access system 100 can include an instrument 300 that is releasably coupled to the retractor body 3 for manipulating the retractor body 3, such as to engage and retract soft tissue with the distal end 6 thereof. The instrument 300 includes a handle 302 that extends along a forward direction FD from a rear end 304 of the instrument 300 to a coupling mechanism 308 at a front end 306 of the instrument 300. The coupling mechanism 300 releasably couples the instrument 300 to the retractor body 3. For example, the coupling mechanism 308 can be configured to iterate between a coupled configuration (shown in FIGS. 4A through 4C), in which the instrument 300 is rigidly coupled to the retractor body 3, and a de-coupled configuration (shown in FIG. 4D), in which the instrument 300 is de-coupled and removable from the retractor body 3, as described in more detail below.

Figure 4C:
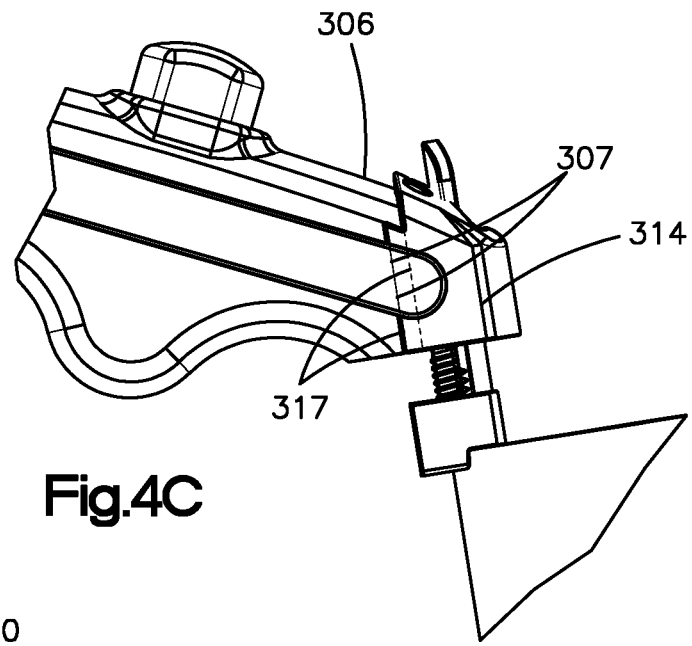
FIG. 4C is a side view of a portion of the instrument illustrated in FIG. 4A, showing a portion of a coupling mechanism of the instrument in the coupled configuration with the attachment device and further showing a proximal mount of the attachment device in the locked configuration with the access member.
Figure 4D:
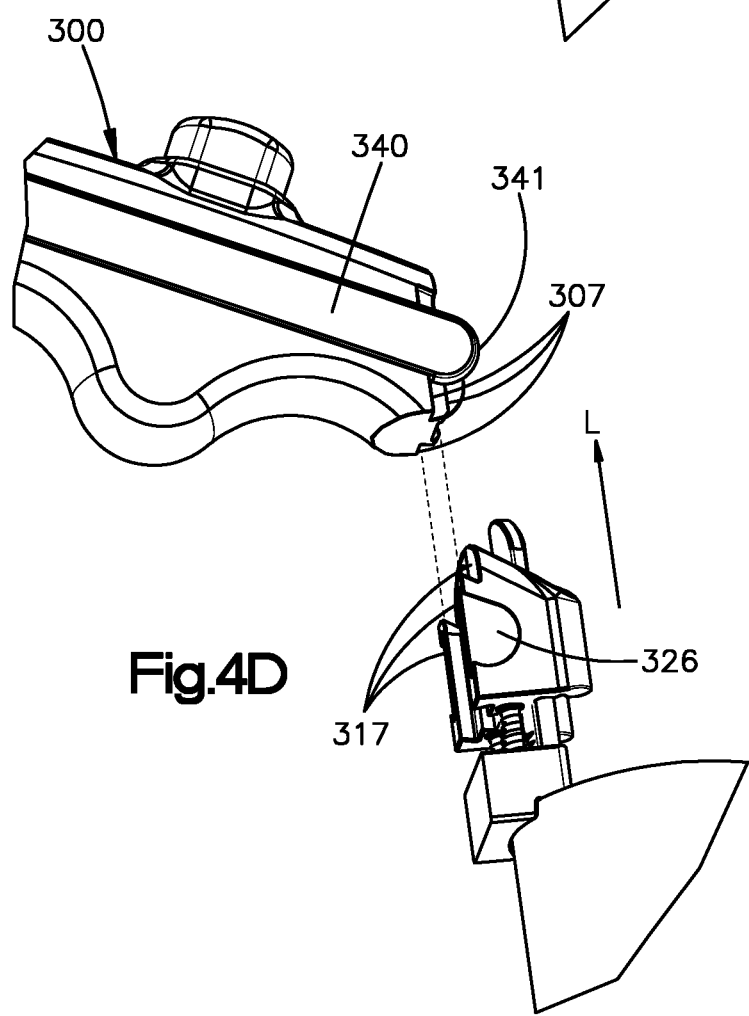
FIG. 4D is a side view of the portion of the instrument illustrated in FIG. 4C, showing the portion of the coupling mechanism in a de-coupled configuration, in which the instrument is uncoupled from the attachment device, further showing the proximal mount remaining in the locked configuration with the access member.

The instrument 300 can also be configured to operate an attachment device 314 coupled to the retractor body 3. As above, the attachment device 314 is configured to attach the retractor body 3 to the access member 102, particularly to the inner wall surface 116 after the distal end 6 of the retractor body 3 has engaged the soft tissue to be retracted thereby. In the present embodiment, the attachment device 314 can have a proximal mount 316 and a distal mount 318 configured to respectively mount to the proximal and distal ends 110, 112 of the access member wall 104. The proximal mount 316 defines one or more mating surfaces 317 configured to engage one or more complimentary mating surfaces 307 defined at the front end 306 of the instrument 300. The mating surfaces 307, 317 can be aligned with the axial and longitudinal directions, respectively, allowing the instrument 300 to lift off of the proximal mount 316 along the longitudinal direction L when in the de-coupled configuration, as shown in FIG. 4D.

Figure 4E:
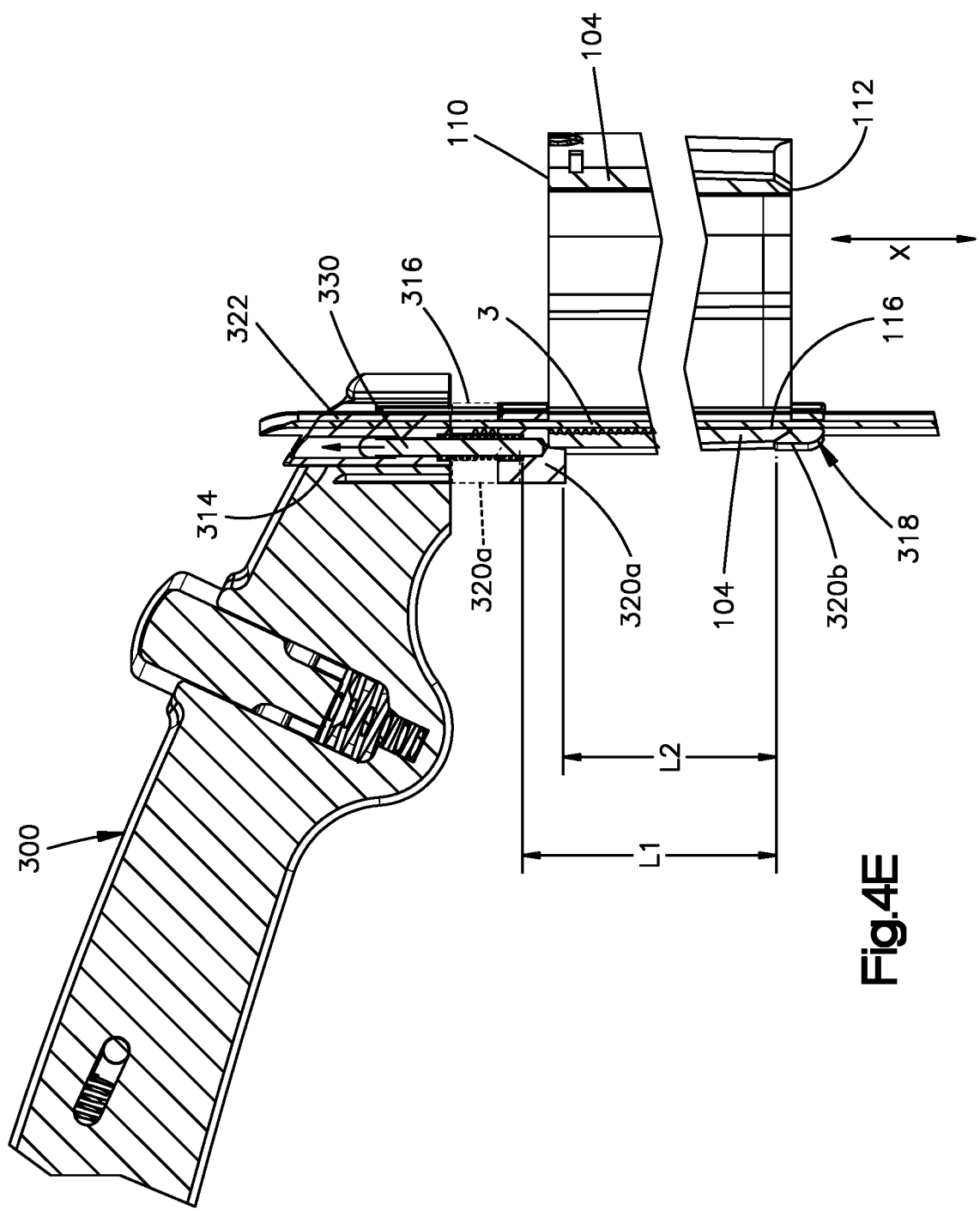
FIG. 4E is a sectional side view of the surgical access system illustrated in FIG. 4A, showing iteration of the proximal mount between the locked configuration and an unlocked configuration with respect to the access member.

Referring now to FIG. 4E, the proximal and distal mounts 316, 318 can each include an engagement member 320a, 320b configured to engage the access member 102, such as at the proximal and distal ends 110, 112 thereof, in a manner securing the attachment device 314 (and thus also the retractor body 3) to the wall 104. As shown, each of the engagement members 320a, 320b can be a hook configured to hook or otherwise latch to the respective proximal and distal ends 110, 112 of the access member 102. Additionally, at least one of the proximal and distal mounts 316, 318, such as the engagement member 320a, 320b thereof, can be configured to move between an unlocked configuration, in which the proximal and distal mounts 316, 318 are longitudinally spaced from each other by a first distance L1, and a locked configuration in which the proximal and distal mounts are longitudinally spaced from each other by a second distance L2 that is less than the first distance L1. In particular, the second distance L2 corresponds to a distance between the proximal and distal ends 110, 112 of the wall 104 along the axial direction X. In this manner, the proximal and distal mounts 116, 118 can be configured to achieve a secure grip against the access member 102 for attaching the retractor body 3 thereto.

The surgical access system 100 includes an actuator 330 configured to actuate the at least one of the proximal and distal mounts 316, 318 from the unlocked configuration to the locked configuration. For example, the proximal mount 316 can include a mount base 322 that is coupled to the engagement member 320a. In the illustrated embodiment, the actuator 330 extends between and connects the mount base 322 and the engagement member 320a together. Additionally, the actuator 330 is configured to actuate longitudinal movement of the engagement member 320a relative to the mount base 322 between the unlocked configuration and the locked configuration.

Referring now to FIG. 4F, the actuator 330 can comprise a bias mechanism 331 for biasing one or both of the proximal and distal mounts 316, 318 into either the locked or unlocked configuration. In the illustrated embodiment, the bias mechanism 331 includes a spring assembly 332 that includes at least one spring 334, such as a pair of springs 334, that applies a bias force on the engagement member 320a away from the mount base 322 in a bias direction, such as the distal direction D, thereby actuating the engagement member 320a to the locked configuration. The spring assembly 332 can also include one or more spring guide members 336, such as a pair of guide rods 336 or dowels, that extend centrally through the springs 334 as shown, and are configured to guide movement of the engagement member 320a toward and away from the mount base 322 along the longitudinal direction L.

The coupling mechanism 308 of the instrument 300 can be configured to move the actuator 330 in a manner causing, or at least contributing to, the actuation of one or both of the proximal and distal mounts 316, 318 between the locked and unlocked configurations. For example, in the illustrated embodiment, the coupling mechanism 308 can include one or more movement members, such as a pair of arms 340, that are configured to be operatively connected to the engagement member 320a of the proximal mount 316 in a manner causing movement of the engagement member 320a relative to the mount base 322, as described in more detail below. As shown, the arms 340 can be spaced from each other along the lateral direction A and can be translatable relative to the handle 302, such as along an arm translation direction having at least a directional component along the forward direction FD and/or a rearward direction RD opposite the forward direction FD. The arms 340 can ride along complimentary guide formations, such as guide slots 342 defined in a body 305 of the handle 302. The guide slots 342 and the arms 340 can have complimentary dovetail geometries, as shown.

Figure 4G:
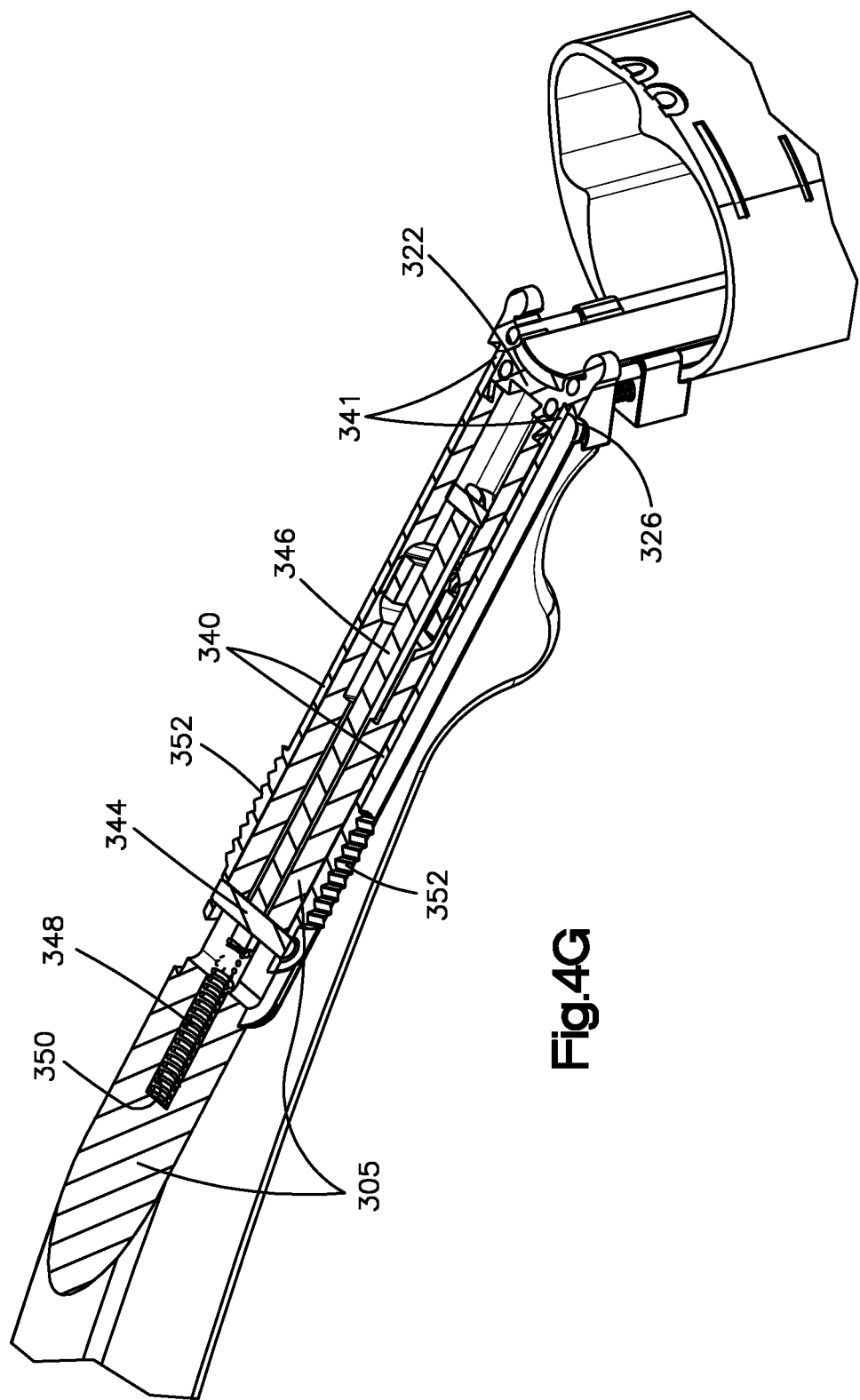
FIG. 4G is a sectional perspective view of the coupling mechanism of the instrument illustrated in FIG. 4A.

Referring now to FIG. 4G, the arms 340 can be coupled together by a yoke member 344, which can also couple the arms 340 to a central arm 346, that is biased along either the forward or rearward directions FD, RD. In the illustrated embodiment, the coupling mechanism 308 includes an arm bias member 348, such as a spring, which can reside in a slot 350 defined centrally within the handle body 305. The bias member 348 depicted is a compression spring that engages the central arm 346 so as to bias it and also arms 340 in the forward direction FD into the coupled configuration with the retractor body 3. In the present embodiment, when in the coupled configuration, distal ends 341 of the arms 340 engage with and couple to the mount base 322, which rigidly couples the instrument 300 to the retractor body 3. As shown, when in the coupled configuration, the distal ends 341 of the arms 340 can extend within complimentary shaped receptacles 326 in the mount base 322 (see also FIG. 4C). The arms 340 are also configured to translate in the rearward direction RD to withdraw the distal end 341 of the arms 340 from the receptacles 326 of the mount base 322, thereby moving the instrument 300 into the de-coupled configuration. In this manner, the arms 340 can be translated in the forward and rearward directions FD, RD to iterate the coupling mechanism 308 between the coupled and de-coupled configurations. Outer surfaces of the arms can include grip enhancement features 352, such as serrations, for facilitating manual retraction of the arms 340. As shown in FIG. 4D, when the distal ends 341 of the arms 340 are remote from the receptacles 326 of the mount base 322, the instrument 300 can be moved away from the attachment device 314, which remains attached to the access member 102.

Figure 4H:
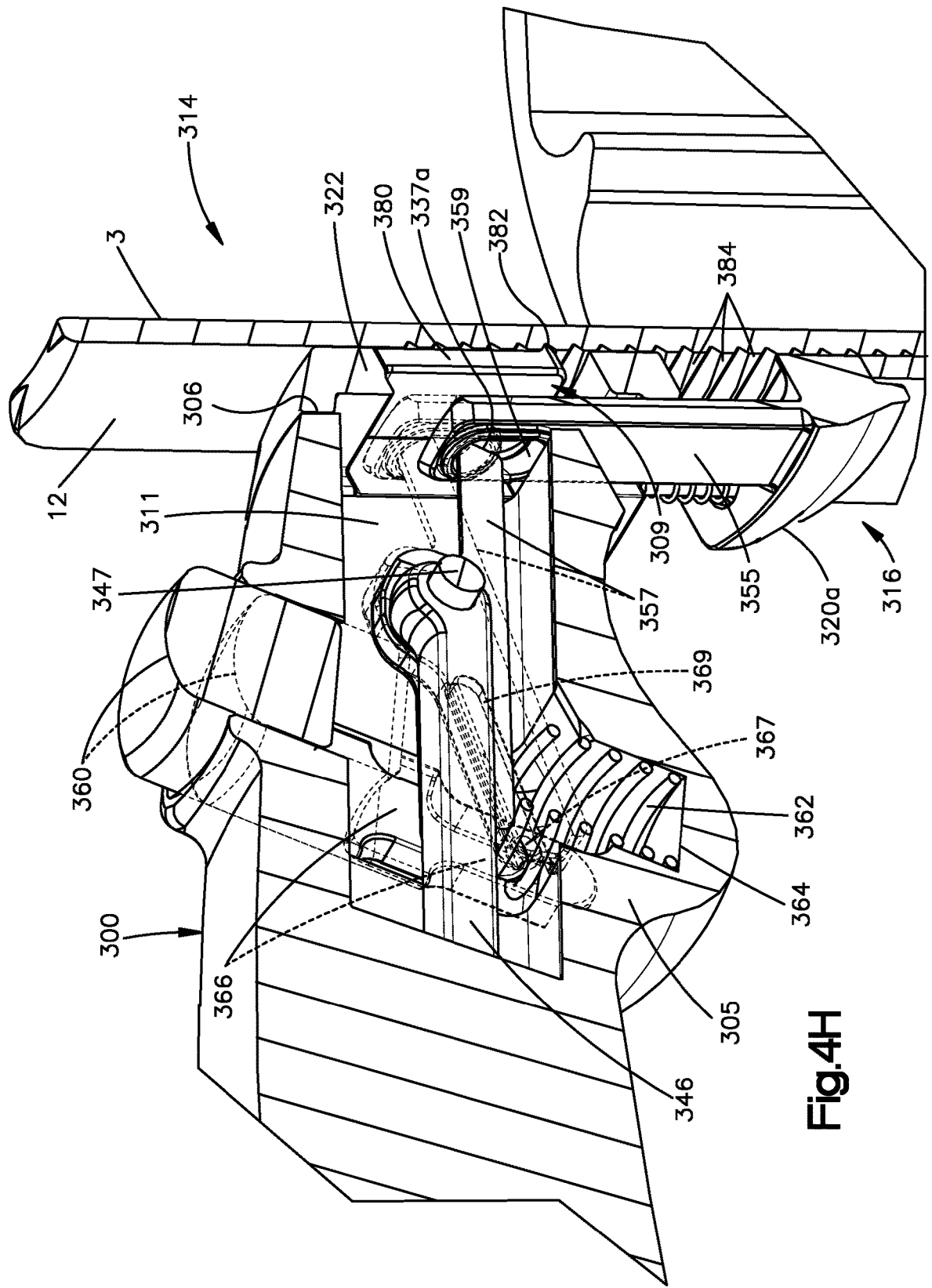
FIG. 4H is a sectional perspective view of the coupling mechanism illustrated in FIG. 4A.

Referring now to FIG. 4H, while the coupling mechanism 308 is in the coupled configuration with the mount base 322, the instrument 300 can also be configured to engage the actuator 330 for moving the engagement member 320a relative to the mount base 322, such as to the unlocked configuration. As shown, the central arm 346 can be operationally connected to a return member 335 of the bias mechanism 331. The return member 335 is configured to move the engagement member 320a toward the mount base 322 in a direction opposite the bias direction, such as the proximal direction P opposite the distal direction D, so as to move the engagement member 320a to the unlocked configuration. The return member 335 can be an elongated member extending proximally from the engagement member 320a of the proximal mount 316 and through an opening 309 at the front end 306 of the instrument 300 and into a chamber 311 defined within the handle body 305. The opening 309 can be defined between the handle body 305 and the base member 322 of the proximal mount 316. The return member 335 can be monolithic with the engagement member 320a, as shown, or can alternatively be a separate member that is connected to the engagement member 320a.

The instrument 300 can include a connector 337 that connects the central arm 346 to the return member 335. A front end 337a of the connector 337 can be configured to reside within a recess 339 defined by the return member 335 when the coupling mechanism 308 is in the coupled configuration, as shown. The front end 337a of the connector 337 and the recess 339 can have complimentary geometries such that the connector 337 retains the return member 335 in the unlocked configuration (against the bias force) when the front end 337a resides in the recess 339. The instrument 300 can include a second actuator, such as a button 360, configured to iterate the engagement member 320a of the proximal mount 316 between the locked and unlocked configurations. The button 360 can be configured to iterate between a first or neutral button position, in which the proximal mount 316 is in the locked configuration, and a second or depressed button position, in which the proximal mount 316 is in the unlocked configuration. In particular, the button 360 can be biased into one of the neutral and depressed button positions by a button bias member, such as a spring 362, which can reside within a button spring receptacle 364 defined within the handle body 305.

The button 360 can include one or more extensions or legs 366, such as a pair of legs 366 that straddle the central arm 346. At least one of the button legs 366 can include a cam protrusion 367 configured to ride along a complimentary groove 369 defined in the connector 337. The connector 337 can be pivotably coupled to the central arm 346 via a pin joint 347, so that as the button 360 is depressed, the cam 367 and groove 369 engagement pivots the connector 337 about the pin joint 347 so that the front end 337a of the connector 337 pulls the return member 335 in the proximal direction P against the bias force, thereby moving the engagement member 320a of the proximal mount 316 to the unlocked configuration. Additionally, as the button 360 iterates to its neutral position, the cam 367 and groove 369 engagement pivots the connector 337 oppositely about the pin joint 347, thereby allowing the bias mechanism 331 to return the engagement member 320a to the locked configuration. Thus, the physician can operate the button 360 to move the proximal mount 316 between the locked and unlocked configurations as needed. It should be appreciated that the front end 337a of the connector 337 is configured to be remote from the receptacle 339 in the rearward direction RD when the instrument 300 is in the de-coupled configuration. Thus, moving the arms 340 in the forward and rearward directions FD, RD to iterate the coupling mechanism 308 between the coupled and de-coupled configurations engages and disengages the connector 337 from the return member 335.

Operation of the instrument 300 to retract soft tissue at the treatment site will now be described. The instrument 300 can be used to insert the retractor body 3 through the working channel 106 to engage and retract soft tissue. In particular, the physician can manipulate the retractor body 3 to engage and retract soft tissue via the handle 302. Once the soft tissue is engaged, the physician can use the instrument 300 to pull the soft tissue toward the wall 104. The design of the attachment device 314 allows the physician to elect whether to first secure the proximal or distal mount 316, 318 to the respective proximal or distal end 110, 112 of the access member 102. The elected mount 316, 318 is secured to the respective end 110, 112 of the access member 102 by engaging the end 110, 112 with the hook 320a, 320b of the mount 316, 318. To secure the elected mount 316, 318 to the respective end 110, 112 of the access member 102, the physician can depress the button 360 to move the engagement member 320 of the proximal mount 316 to the unlocked configuration. It should be appreciated that, with one of the mounts 316, 318 secured, the physician can optionally use the secured mount 316, 318 as a pivot or fulcrum to bring the other of the proximal and distal mounts 316, 318 into alignment with the respective end 110, 112 of the access member 102. With both mounts 316, 318 aligned with the ends 110, 112 of the access member 102, the physician can then release the button 360, thereby allowing the bias mechanism 331 to bias the proximal engagement member 320a away from the mount base 322 in a manner reducing the longitudinal distance between the mounts 316, 318 until both mounts 316, 318 are secured to the ends 110, 112 of the access member 102 in the locked configuration.

Referring now to FIGS. 4I through 4K, the attachment device 314 can be configured to allow translation of the retractor body 3 along the longitudinal direction L relative to the access member 102 while attached to the wall 104. For example, the attachment device 314 can include one or more elongate member 370, such as a pair of rods, that extend within the working channel 106 from the proximal mount 316 to the distal mount 318. The rods 370 are spaced from each other along the lateral direction A so that the retractor body 3 can extend between the rods 370. One or both of the proximal and distal mounts 316, 318 can include guide features, such as guide shoes 372 that engage the lateral sides 20, 22 of the retractor body 3. For example, the guide shoes 372 and the lateral sides 20, 22 of the retractor body 3 can have complimentary shapes to guide translation of the retractor body 3 along the longitudinal direction L. One or both of the proximal and distal mounts 316, 318 can also define a guide channel 374 having a complimentary geometry with the retractor body 3 for further guiding its translational movement 3 along the longitudinal direction L.

The attachment device 314 can include a retention mechanism for retaining the relative longitudinal position between the retractor body 3 and the attachment device 314. For example, as shown in FIG. 4H, the base member 322 can include a flexible tab or pawl 380 having a tooth 382 at a distal, free end of the pawl 380. The tooth 382 is configured to successively engage a longitudinal series of complimentary ratchet grooves 384 defined in the outer surface 12 of the retractor body 3 as the retractor body 3 translates relative to the mount base 322. The tooth 382 and ratchet grooves 384 can have complimentary geometries that allow the physician to manually translate the retractor body 3 longitudinally relative to the attachment device 314 as desired, yet provide sufficient resistance to retain the relative longitudinal position between the retractor body 3 and the attachment device 314 after the physician ceases manipulating the retractor body 3. It should be appreciated that the complimentary geometries of the tooth 382 and ratchet grooves 384 can be tailored as needed to provide a desired amount of resistance to relative longitudinal movement between the attachment device 314 and the retractor body 3.

Figure 5A:
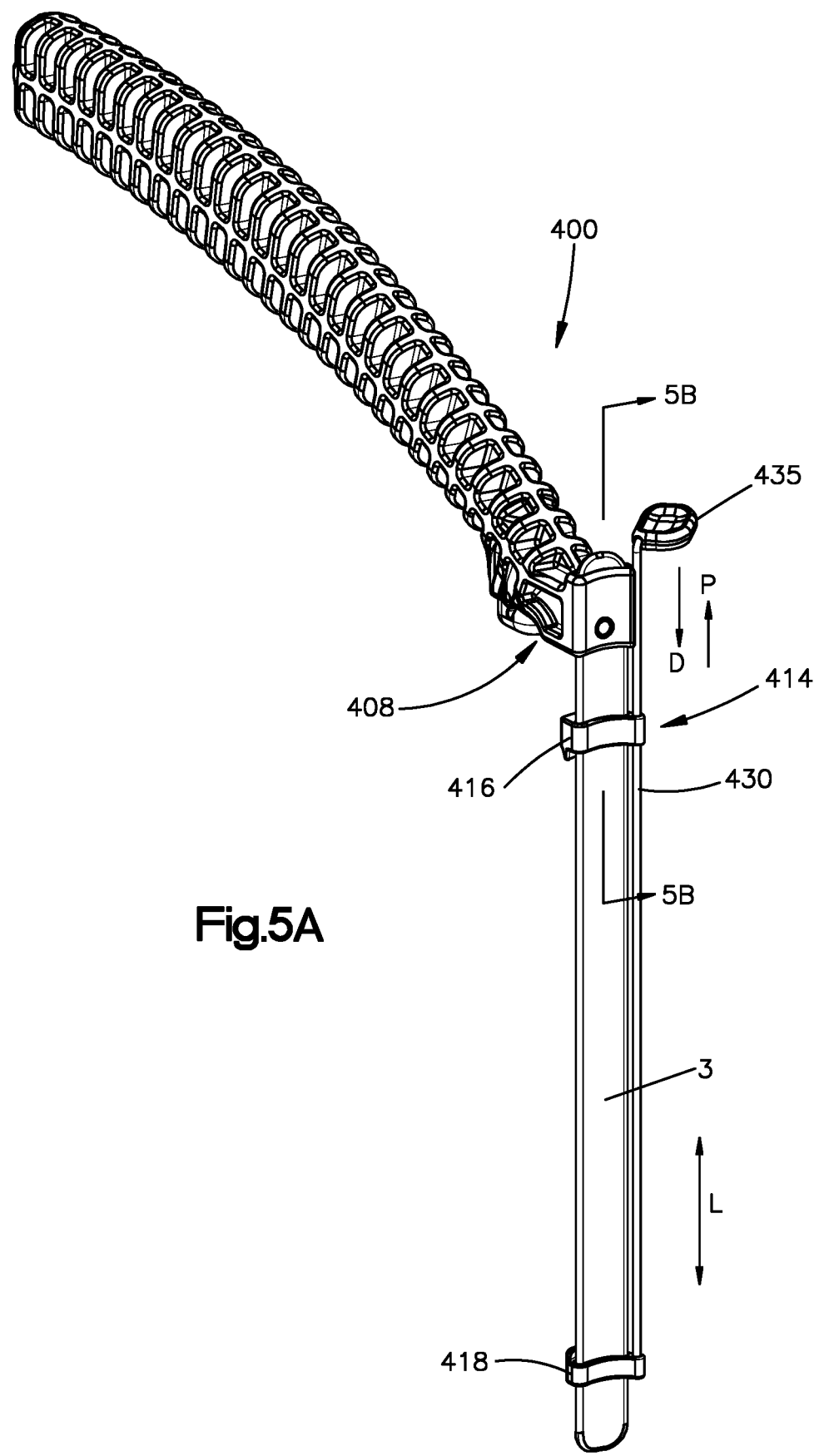
FIG. 5A is a perspective view of another embodiment of an instrument releasably coupled to a retractor, in which the instrument couples directly to the retractor, the retractor carries an attachment device for attaching the retractor to a select circumferential location of the access member, and the attachment device is operable independently from the instrument.

Referring now to FIG. 5A, another embodiment of the surgical access system 100 is shown that includes an instrument 400 that is releasably coupled to the retractor body 3. As with the embodiments described above, the instrument 400 is configured to iterate between a coupled configuration, in which the instrument is coupled to the retractor body 3, and a de-coupled configuration, in which the instrument 400 is de-coupled and removable from the retractor body 3. For the sake of brevity, the following disclosure will focus on differences between this embodiment and the embodiment described above with reference to FIGS. 4A through 4K.

In the present embodiment, the retractor body 3 carries an attachment device 414 that is operable between a locked configuration and an unlocked configuration independent of operation of the instrument 400. As shown, the attachment device 414 includes proximal and distal mounts 416, 418 that can each have a hook-like geometry for engaging the proximal end distal ends 110, 112 of the access member 102. An elongate actuator 430 extends proximally from the distal mount 418, through a receptacle defined by the proximal mount 416, and to a control member 435 that is spaced from the proximal mount 416 in the proximal direction P. The elongate actuator 430 can be a rod that can be rigidly coupled to the distal mount 418 and configured to slide the distal mount 418 along the retractor body 3 and relative to the proximal mount 416 so as to adjust the longitudinal distance between the proximal and distal mounts 416, 418 as needed to attach to the access member 102. The control member 435 can be a finger tab allowing push-push operation of the elongate actuator 430 along the longitudinal direction L.

The instrument 400 can be used to insert the retractor body 3 through the working channel 106 to engage and retract soft tissue. As above, once the soft tissue is engaged, the physician can use the instrument 400 to pull the soft tissue toward the wall 104, electing to secure either the proximal or distal mount 416, 418 to the respective proximal or distal end 110, 112 of the access member 102 first by hooking the end 110, 112 with the hook of the mount 416, 418. From this position, the physician can align the other of the proximal and distal mounts 416, 418 with the respective end 110, 112 of the access member 102, and then operate the control member 435 to reduce the longitudinal distance between the mounts 416, 418 until both mounts 416, 418 are secured to the ends 110, 112 of the access member 102 in the locked configuration. The proximal and distal mounts 316, 318 preferably each define a guide channel 474 (shown in FIG. 5B) having a complimentary geometry with the retractor body 3 for further guiding translational movement of the retractor body 3 along the longitudinal direction L, at least after the instrument 400 is de-coupled from the attachment device 414.

Figure 5B:
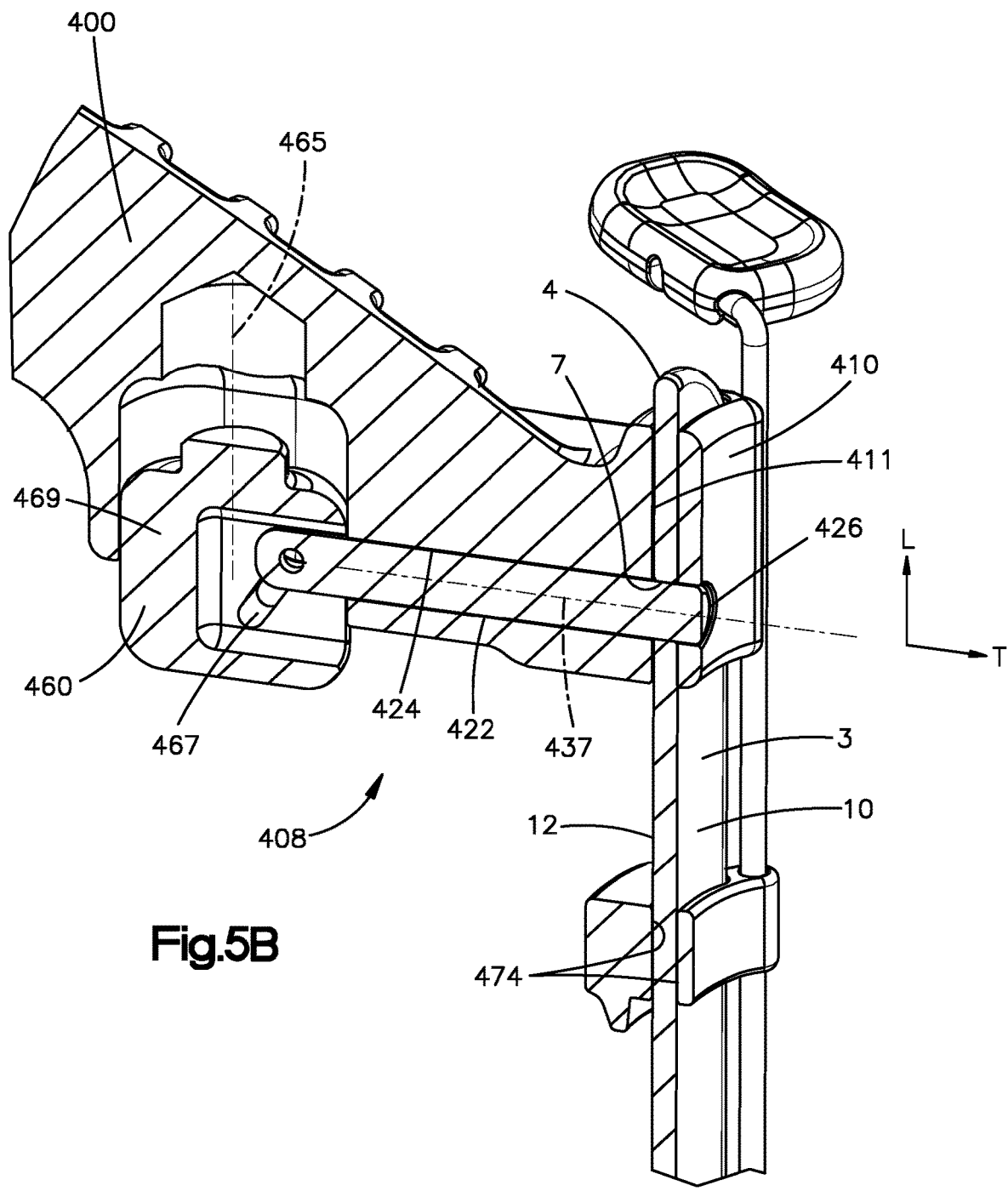
FIG. 5B is a sectional perspective view of a coupling mechanism of the instrument taken along section line 5B-5B illustrated in FIG. 5A.

Referring now to FIG. 5B, the instrument 400 includes a coupling mechanism 408 that couples directly to the retractor body 3. In particular, the instrument 400 has an instrument body 405 having a mounting sleeve 410 at a front end 406 thereof. The mounting sleeve 410 defines a receptacle 411 that is configured to receive a proximal portion of the retractor body 3 along the proximal direction P. Additionally, the coupling mechanism 408 includes a locking pin 422 that resides within a pin receptacle 424 defined within the instrument body 405 along a pin axis 435. The pin axis 425 can be oriented along the transverse direction T. The pin receptacle 424 is aligned with a locking hole 426 defined within a front portion of the mounting sleeve 410. In the present embodiment, the retractor body 3 defines a locking aperture 7 extending from the inner surface 10 to the outer surface 12 along the transverse direction T. The proximal end 4 of the retractor body 3 can be inserted along the proximal direction P within the mounting sleeve 410 until the locking aperture 7 is aligned with the locking pin 422. Once aligned, the locking pin 422 can be advanced from a de-coupled configuration, in which the pin 422 is remote from the locking aperture 7, to a coupled configuration, in which the locking pin 422 extends through the locking aperture 7 of the retractor body 3 and into the locking hole 426.

The locking pin 422 can be iterated between the coupled and de-coupled configurations by movement of a button 460 between a first button position and a second button position along a button axis 465. The button axis 465 can be oriented at an angle relative to the pin axis 425. As shown, the button 460 and the pin 422 can define a complimentary camming mechanism, which can include a side pin or protrusion extending laterally from the pin 422 and into a cam groove 467 defined in a body 469 of the button 460. In this manner, iterative motion of the button 460 along its axis 465 can drive iterative motion of the locking pin 422 along its axis 425 between the coupled and de-coupled configurations. It should be appreciated that a biasing member, such as a spring, can extend between the button 460 and the instrument body 305, which can be operated in complimentary fashion with the camming mechanism to effectively toggle the locking pin 422 between the coupled and de-coupled configurations.

Referring now to FIGS. 6A through 6F, the instrument 400 described above can be configured to employ a tensile actuator, such as a suture member 431, for pulling the distal mount 418 toward the proximal mount 416 and moving the attachment device 414 into the locked configuration. In such embodiments, the distal mount 418 can include one or more receiving formations for receiving at least a portion of the suture member 431. Such receiving formations can include one or more apertures 470 defined by the distal mount 418, such as a pair of apertures 470 that are spaced apart from each other along the lateral direction A. The pair of apertures 470 can extend through a rear portion of the distal mount 418 along a direction having at least a directional component along the transverse direction T. The suture member 431 can be threaded through the apertures 470 so as to define one or more suture tails 434, such as a pair of suture tails 434, which can be operatively coupled to the proximal mount 416. The proximal mount 416 can include one or more additional receiving formations 437, such as suture channels, cleats, and the like, for receiving and securing the one or more suture tails 434 thereto. The instrument 400 can also include additional receiving formations, such as channels, cleats, and the like, for receiving and/or securing free end(s) of the one or more suture tails 434 extending from the proximal mount 416, allowing the physician to tighten the one or more suture tails 434 relative to the instrument 400 in a secure, yet unlocked configuration.

Figure 6A:
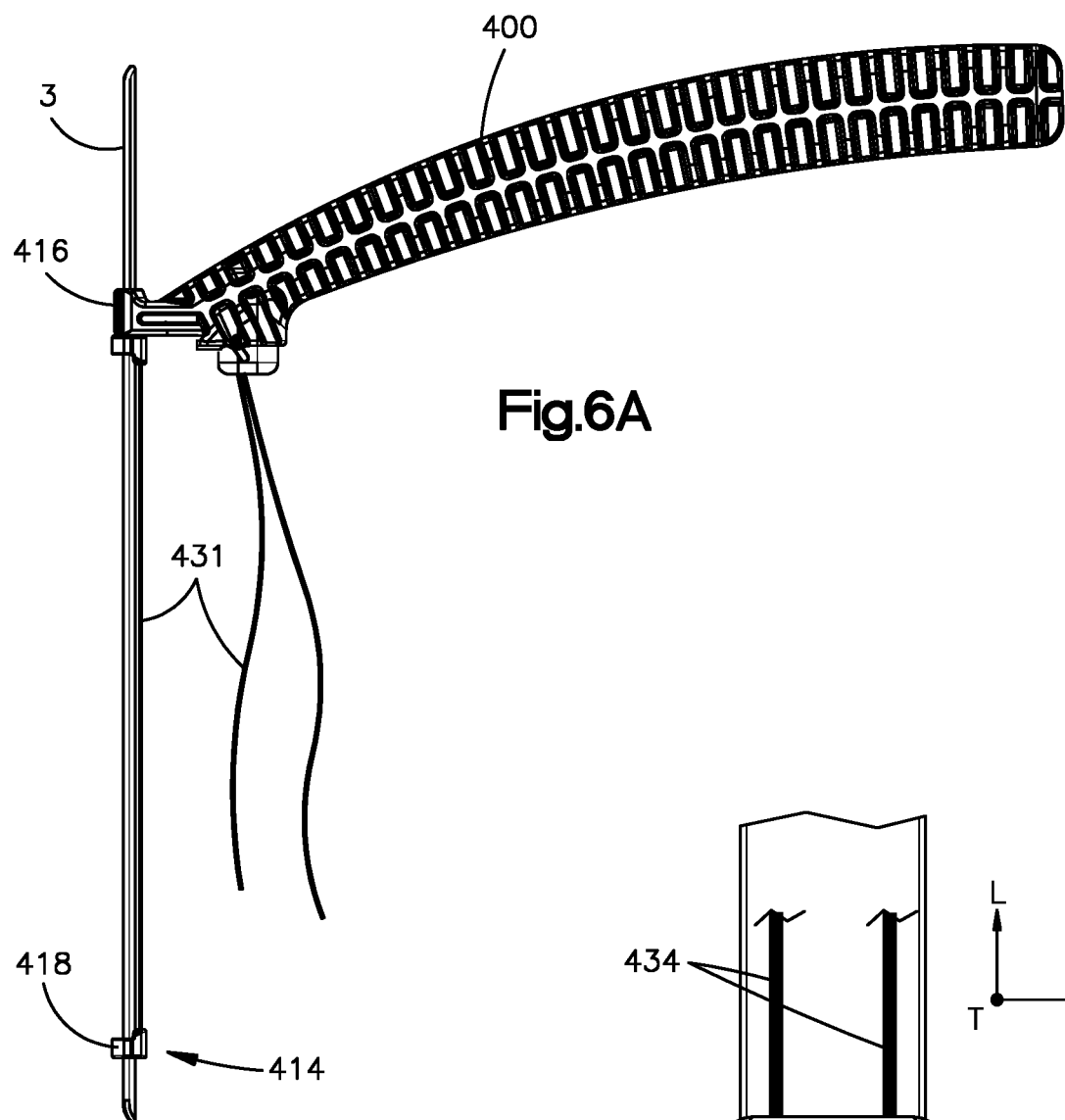
FIG. 6A is a side plan view of another embodiment of an instrument releasably coupled to a retractor, in which the retractor includes an attachment device that employs a tensile actuator for attaching the retractor to a select circumferential location of the access member.
Figure 6B:
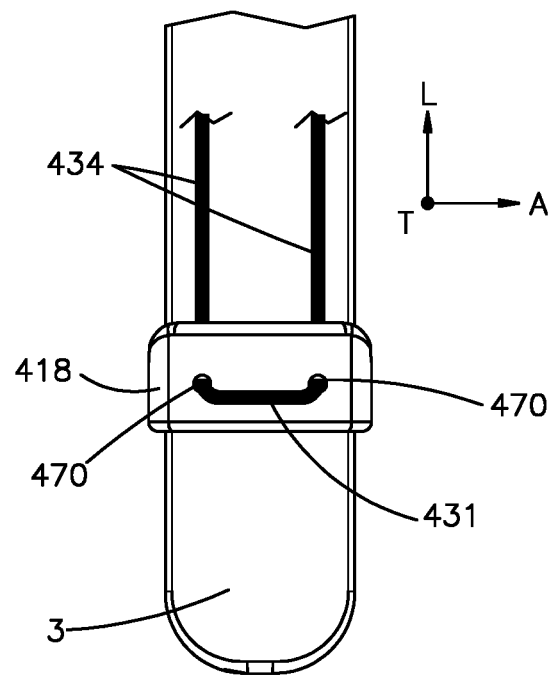
FIG. 6B is a rear plan view of a distal mount of the attachment device illustrated in FIG. 6A, in which the distal mount is actuated by the tensile actuator.
Figure 6C:
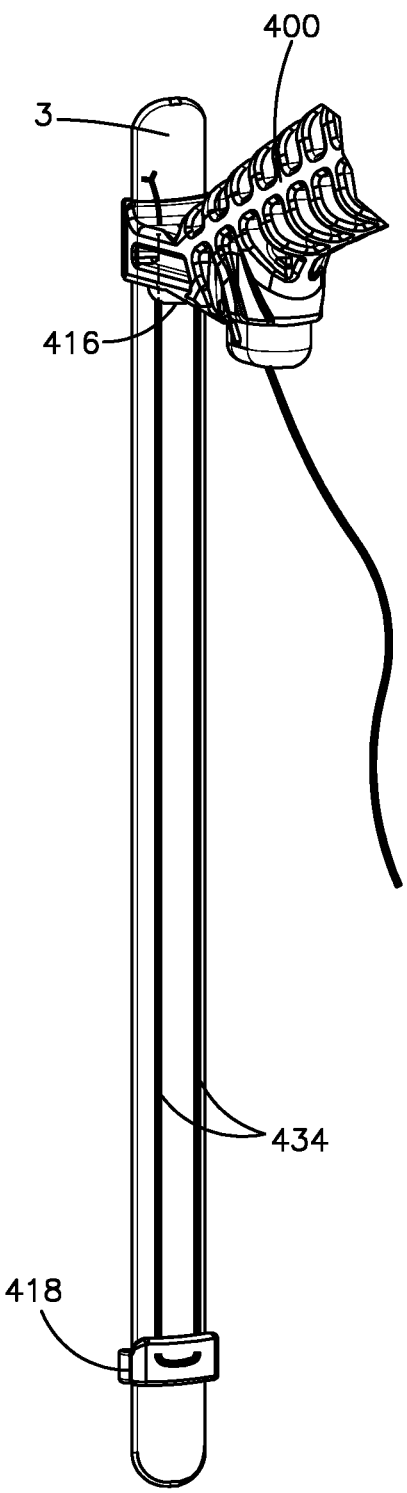
FIG. 6C is a perspective view of the attachment device illustrated in FIG. 6A.
Figure 6D:
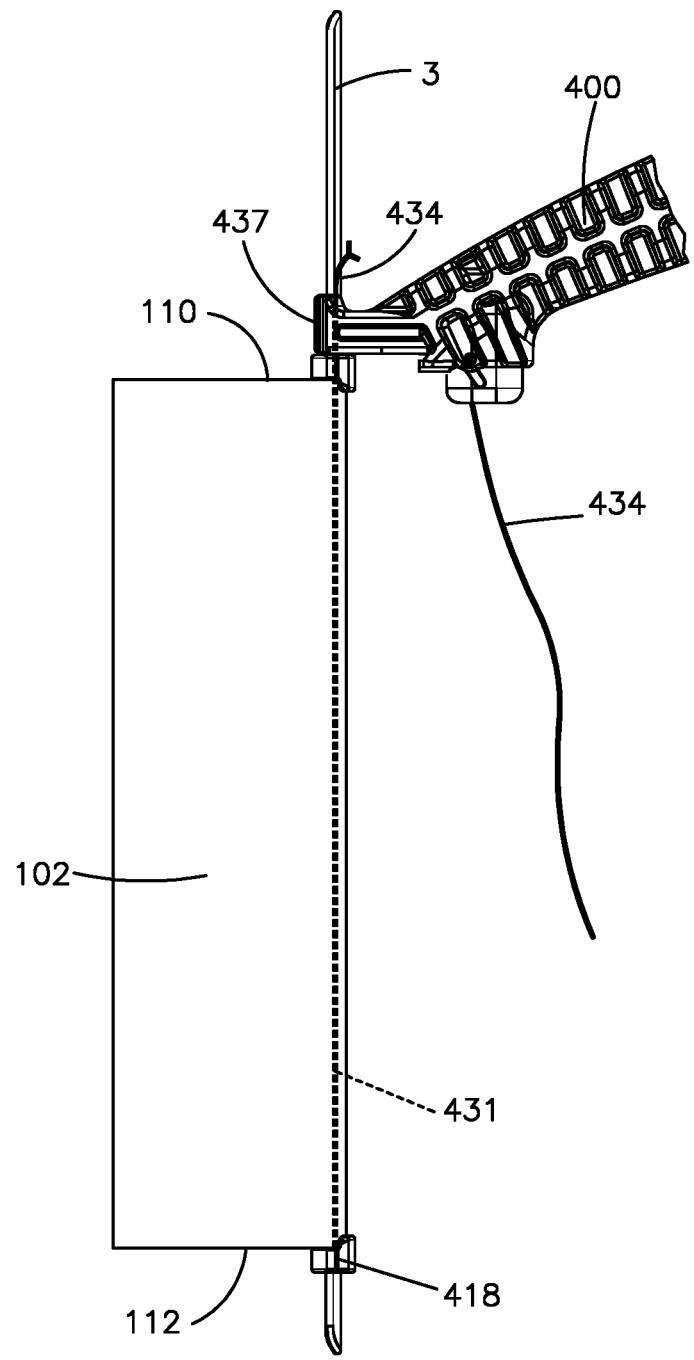
FIG. 6D is a side plan view of a surgical access system, showing the instrument, retractor, and attachment device of FIG. 6A attached to an access member.
Figure 6E:
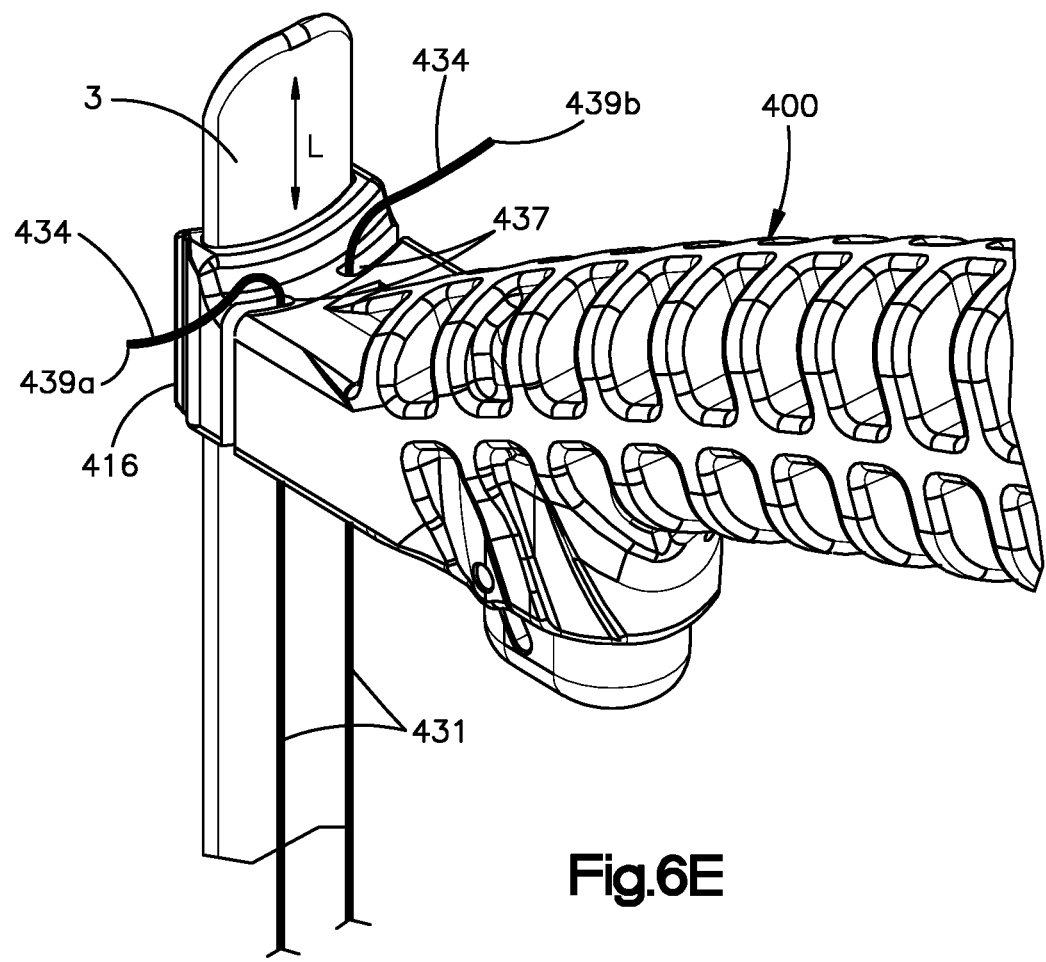
FIG. 6E is a perspective view of a proximal mount of the attachment device illustrated in FIG. 6A, showing the proximal mount having receiving formations for receiving the tensile actuator.

As shown in FIG. 6E, the one or more receiving formations 437 of the proximal mount 416 can be configured so that the respective suture tail 434 can lock therewith via friction. The suture member 431 can extend from a first end 439a thereof, through a first receiving formation 437 at the proximal mount 416, alongside the retractor body 3 along the longitudinal direction L, through the apertures 470 in the distal mount 418, alongside the retractor body 3 again and back toward the proximal mount 416, through a second receiving formation 437 at the proximal mount 416, and to a second end 439b of the suture member 431 opposite the first end 439a. In this manner, the suture tail 434 adjacent the second end 439b can be manipulated by the physician to tension the suture member 431 to pull the distal mount 418 toward the proximal mount 416, thereby moving the attachment device 414 into the locked configuration. Once in the locked configuration, the suture tail 434 adjacent the second end 439b can be secured to the second receiving formation 437, thereby locking the attachment device 414 in the locked configuration. It should be appreciated that the first end 439a of the suture member 431 can be tied or otherwise configured in a knot for retaining the first end 439a at the first receiving formation 437. Moreover, the second end 439b of the suture member 431 can optionally be coupled to a pull member, such as a rigid ring or loop, for assisting the physician in tensioning the suture member 431.

In the unlocked configuration, the instrument 400 can be used to insert the retractor body 3 through the working channel 106 to engage and retract soft tissue. Once the soft tissue is engaged, the physician can use the instrument 400 to pull the soft tissue toward the wall 104. During this process, the physician can elect to secure at least one of the proximal and distal mounts 416, 418 to the respective proximal and/or distal end 110, 112 of the access member 102, such as by hooking the end with the hook of the mount 416, 418. As above, the design of the attachment device 414 allows the physician to hook either the proximal mount 416 or the distal mount 418 to the respective end 110, 112 first. From this position, the physician can align the other of the proximal and distal mounts 416, 418 with its respective end of the access member 102, and then apply a tensile force to the suture member 431, such as by pulling the free suture tail 434 adjacent the second end 439b, until the proximal and distal mounts 416, 418 are secured to the ends 110, 112 of the access member 102 in the locked configuration, as shown in FIG. 6D. From this position, the physician can affix the free suture tail 434 to the second receiving formation 437 of the proximal mount 416 (so that both suture 434 are secured to the proximal mount 416), thereby maintaining the mounts 416, 418 in the locked configuration. The physician can also detach one or both of the ends 439a, b of the suture tails 434 from the receiving formations of the instrument 400, allowing the instrument 400 to de-couple from the proximal mount 416 with the proximal and distal mounts 416, 418 secured in the locked configuration.

Figure 6F:
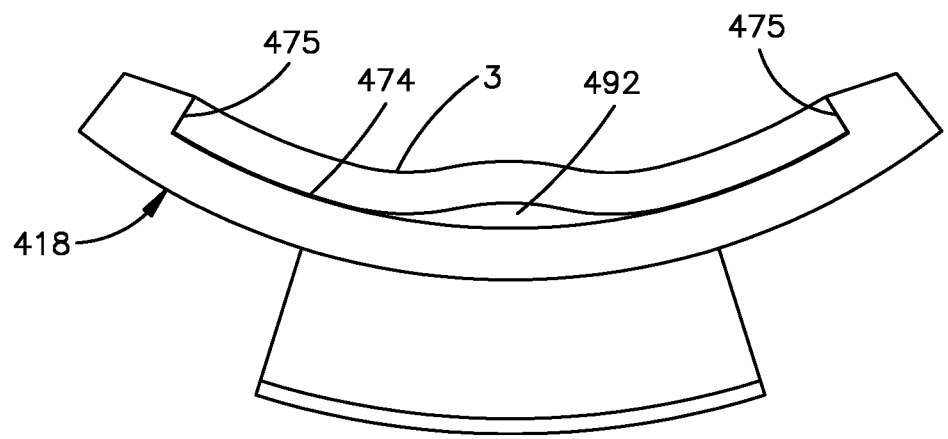
FIG. 6F is a bottom plan view of the distal mount and the retractor blade illustrated in FIG. 6B.

Similarly as described above, the proximal and distal mounts 416, 418 preferably each define a guide channel having a complimentary geometry with the retractor body 3 for guiding translational movement of the retractor body 3 along the longitudinal direction L relative to the mounts 416, 418 after the instrument 400 is de-coupled from the proximal mount 416. For example, as shown in FIG. 6F, one or both of the proximal and distal mounts 416, 418 can define a channel 474 with keystone-like channel sidewalls 475 that retains the retractor body 3 within the channel 474 while allowing longitudinal translation of the retractor body 3 relative to the mount. Additionally, the outer surface 12 of the retractor body 3 can optionally define a longitudinal channel or groove 492 configured to receive the suture member 431. It should also be appreciated that the instrument 400 of the present embodiment can employ the same or a similar coupling mechanism as the coupling mechanism 408 described above with reference to FIG. 5B for selectively coupling directly to and de-coupling from the retractor body 3. In such embodiments, the proximal mount 416 can be rigidly affixed to the mounting sleeve 410 of the coupling mechanism. It should further be appreciated that in additional embodiments the instrument 400 described above with reference to FIGS. 6A through 6F can be configured to employ a tensile actuator that is alternatively an elastic member, such as an elastic band, by way of a non-limiting example.

Referring now to FIGS. 7A through 7C, the surgical access system 100 can include an attachment device 714 having proximal and distal mounts 716, 718 and employing a retention mechanism, such as a ratchet or ratchet-like mechanism, for securing the mounts 716, 718 in the locked configuration to the access member 102. Similar to the embodiments described above with reference to FIGS. 4A through 6D, one or both of the proximal and distal mounts 716, 718 of the present embodiment are configured to iterate between unlocked and locked configurations. Additionally, as above, the mounts 716, 718 include engagement members 720a, 720b, such as hooks, that are configured to hook, latch, or otherwise secure to the respective proximal and distal ends 110, 112 of the access member 102 when in the locked configuration. For the sake of brevity, the following disclosure will focus on differences between the present embodiment and the embodiments described above with reference to FIGS. 4A through 6D.

As shown in FIG. 7A, each of the proximal and distal mounts 716, 718 can include an elongate body portion 719 that is elongated along the longitudinal direction L and conformally shaped with the outer surface 12 of the retractor body 3 for guiding translational movement of the retractor body 3 relative to the mounts 716, 718. The elongate body portions 719a, 719b are configured to extend within the working channel 106 and reside between the retractor body 3 and the inner wall surface 116 of the access member 102. The proximal mount 716 can also include an elongate handle portion 702 that extends from the elongate body portion 719a and is configured to allow a physician to manipulate the retractor body 3 for engaging soft tissue at the treatment site. For example, the elongate handle portion 702 can be configured for manipulation by the physician's index finger. As shown in FIG. 7B, the handle portion 702 can have a circular shape in other embodiments. In yet other embodiments, the handle portion 702 can be configured to deflect between at least one of the elongate (FIG. 7A) and circular (FIG. 7B) configurations to the other configuration.

The attachment device 714 includes an elongate actuator 730 that extends proximally from the distal mount 718, through and/or alongside the proximal mount 716, and to a control member 735 that is spaced from the proximal mount 716 in the proximal direction P. As shown, the elongate actuator 430 can be a pair of rods 731 that can be rigidly coupled to the distal mount 718 and configured to translate the distal mount 718 along the retractor body 3 and relative to the proximal mount 716 to iterate the mounts 716, 718 between the locked and unlocked configurations, similarly as described above with reference to FIG. 5A. As above, the control member 735 can be a finger tab allowing push-push operation of the actuator rods 731 along the longitudinal direction L. For example, the control member 735 can be configured for manipulation by the physician's thumb, while the handle portion 702 is configured for manipulation by the physician's index finger. As shown in FIG. 7C, the actuator rods 731 can extend through guide channels 737 defined in the outer surface 12 of the retractor body 3. The actuation rods 731 can also extend through complimentary guide channels 739 defined by the elongate body portion 719a of the proximal mount 716. In this manner, the actuator rods 731 can translate the distal mount 716 relative to the proximal mount 716.

Referring now to FIGS. 7D and 7E, the retractor body 3 and the proximal and distal mounts 716, 718 can include guide features for guiding translational movement of the retractor body 3 relative to the mounts 716, 718 and vice versa, such as for translating the retractor body 3 relative to the access member 102. For example, the retractor body 3 can define a slot 740 elongate along the longitudinal direction L. The mounts 716, 718 can each include slide members 742 that extend from the respective elongate body portion 719a, 719b and within the slot 740 and are configured to ride longitudinally along the slot. Within the slot 740, the retractor body 3 can define side walls 744 that are canted inwardly toward each other, and the slide members 742 can have a flared geometry that is complimentary with the canted geometry of the side walls 744 in dovetail fashion. In this manner, the sidewalls 744 can retain the slide members 742 within the slot 740, thus also retaining the proximal and distal mounts 716, 718 in engagement with the outer surface 12 of the retractor body 3.

Referring now to FIGS. 7F through 7H, the retention mechanism for selectively retaining the relative longitudinal position between the proximal and distal mounts 716, 718 will now be described. The retractor body 3 can define, for example, a series of ratchet grooves 750 that are arranged longitudinally alongside the slot 740 and are configured to engage at least one complimentary ratchet tooth 752 of at least one of the proximal and distal mounts 716, 718. The ratchet grooves 750 can be defined in the outer surface 12 of the retractor body 3, and can also be at least partially defined by the sidewalls 744 within the slot 740.

As shown in FIGS. 7G and 7H, the ratchet tooth 752 can extend from a flexible tab 754, which can also be referred to as a "pawl", and which can be defined by the elongate body portion 719a of the proximal mount 716. The ratchet tooth 752 is configured to selectively engage at least one and up to each of the ratchet grooves 750 in succession as the proximal mount 716 translates longitudinally relative to the retractor body 3. The ratchet tooth 752 can be located at a first end 756 of the pawl 754 opposite a second end 758 of the pawl 754. The second end 758 can include the hook 320a of the proximal mount 716. The pawl 754 can reside within a recess of cutout 760 defined by the elongate body portion 719a. The pawl 754 can be connected to a remainder of the elongate body portion 719a by a pair of arms 762 opposite each other along the lateral direction A. The pair of arms 762 can provide the pawl 752 with flexibility for rotation along a plane defined by the longitudinal and transverse directions T. In this manner, the pawl 754 can be configured to iterate between a neutral or engaged configuration (as shown in FIG. 7G), in which the tooth 752 resides within one of the ratchet grooves 750 so as to retain a relative longitudinal position between the proximal mount 716 and the retractor body 3, and a flexed or disengaged configuration, in which the tooth 752 is remote from each of the ratchet grooves 750.

The tooth 752 and ratchet grooves 750 can have complimentary geometries that provide substantially equivalent resistance to proximal or distal movement of the proximal mount 716 relative to the retractor body 3. It should be appreciated that the complimentary geometries of the tooth 752 and ratchet grooves 750 can be tailored as needed to provide a desired amount of resistance to relative longitudinal movement between the proximal mount 716 and the retractor body 3. In other embodiments, the tooth 752 and ratchet grooves 750 can have complimentary geometries that prevent proximal movement of the proximal mount 716 relative to the retractor body 3 in the engaged configuration. In such embodiments, the pawl 754 can optionally include a disengagement feature for manually rotating the pawl 754 to the disengaged configuration. It should be appreciated that the retention mechanism of the foregoing embodiments can provide audible and/or tactile feedback regarding relative longitudinal movement between the proximal mount 716 and the retractor body 3 as the tooth 752 successively "clicks" into and out of the ratchet grooves 750. It should be appreciated that in other embodiments, controlled movement of the proximal and distal mounts 716, 718 relative to one another can employed in a friction-based retention mechanism.

Operation of the retractor 2 of the present embodiment will now be described. The handle portion 702 can be used to insert the retractor body 3 through the working channel 106 to engage and retract soft tissue. Once the soft tissue is engaged, the physician can use the handle portion 702 to pull the soft tissue toward the wall 104, electing to secure either the proximal or distal mount 716, 718 to the respective proximal or distal end 110, 112 of the access member 102 first by hooking the end 110, 112 with the hook of the mount 716, 718. From this position, the physician can align the other of the proximal and distal mounts 716, 718 with the respective end 110, 112 of the access member 102, and then operate the control member 735 to reduce the longitudinal distance between the mounts 716, 718, thereby causing the ratchet tooth 752 to sequentially engage the ratchet grooves 750, until both mounts 716, 718 are secured to the ends 110, 112 of the access member 102 in the locked configuration.

It should be appreciated that each of the embodiments described above with reference to FIGS. 4A through 7H, in which the respective attachment devices 314, 414, 714 attach to the ends 110, 112 of the access member 102, allow multiple retractors 2 to be attached concurrently to various select circumferential locations of the access member 102.

Referring now to FIGS. 8A through 8C, the surgical access system 100 can include a suction attachment device 814 configured to selectively attach the retractor body 3 to a circumferential portion of the inner wall 116 of the access member 102. For example, the retractor body 3 can define an internal chamber 816 in fluid communication with a plurality of vacuum ports 818 defined in the outer surface 12 of the retractor body 3. The internal chamber 816 is also in fluid communication with a proximal port 820 that is connectable to a tube 822 that is in turn connectable to a vacuum source 824, such as a vacuum pump. A plurality of ring seals 826 are located in the vacuum ports 818 and are configured to provide sealing engagement with the inner wall surface 116 when the ring seals 826 are brought into contact with the inner wall surface 116 and the vacuum source 824 supplies vacuum pressure to the internal chamber 816 and thus also to the vacuum ports 818. The suction attachment device 814 can be configured to provide a tailored sufficient suction force allowing the retractor body 3 to translate at least longitudinally relative to the access member 102 while the retractor body 3 remains attached to the access member 102 via the suction attachment device 814. It should be appreciated that the present embodiment allows multiple retractors 2 to be attached via suction concurrently to various select circumferential locations of the inner wall surface 116.

Referring now to FIGS. 9A through 9C, the surgical access system 100 can include an attachment device 914 that employs mating engagement between protrusions 920 and openings 922 for selectively attaching the retractor body 3 to a circumferential portion of the access member 102. For example, at least one of the inner wall surface 116 and the retractor body 3 can define one or more openings 922, and the other of the inner wall surface 116 and the retractor body 3 can comprise one or more protrusions 920 that are complimentary with the one or more openings 922. Stated differently, the one or more protrusions 920 are configured for insertion within the one or more openings 922 so as to couple the retractor body 3 to the access member 102.

As shown in FIG. 9A, the wall 104 of the access member 102 can define an array 924 of openings 922 and the retractor 2 can include a series of protrusions 920 for engagement within selective ones of the openings 922. The protrusions 920 can be defined by, and monolithic with, the retractor body 3, or can be carried by an insert connectible with the retractor body 3. The protrusions 920 extend outwardly from the outer surface 12 of the retractor body 3 and are aligned with each other along the longitudinal direction L. The openings 922 can each extend outwardly into the wall from the inner surface 116 thereof. The array 924 can include one or more columns 926 of openings 922 and one or more rows 928 of openings 922. In each column 926, the openings can be aligned with each other along the longitudinal direction L. Thus, each column 926 can be characterized as defining a longitudinally aligned subset of the openings 922 in the array 924. The columns 926 are circumferentially spaced from each other along the wall 104. In each row 928, the openings 922 can be aligned along the lateral direction A. Thus, each row 928 can be characterized as defining a laterally aligned subset of the openings 922 in the array 924. The rows 928 are spaced from each other along the axial direction X of the access member 2 (and also along the longitudinal direction L of the retractor 2 when the retractor 2 is attached to the access member 102). In the embodiment illustrated in FIG. 9A, the protrusions 920 are configured for insertion within any one of columns 926 to selectively attach the retractor body 3 to a circumferential portion of the access member 102. It should be appreciated that the retractor 2 can have fewer protrusions 920 than the number of openings 922 in a column 926. In such embodiments, the retractor 2 can also be selectively attached to the access member 102 at a select depth (i.e., select longitudinal location).

The protrusions 920 can optionally define a stem 930 extending from the retractor 2 and a head 932 located at an outer end of the stem 930 and being wider than the stem 930. As shown in FIG. 9B, the openings 922 can extend radially through the wall 104 from the inner wall surface 116 to the outer wall surface 114. In such embodiments, the protrusions 920 can be configured such that the stems 930 extend through the openings 922 and at least portions of the heads 932 are located radially outward of the outer wall surface 114 when the retractor body 3 is attached to the access member 102. As shown, the stems 930 can be sufficiently long so that the entire head 932 is located radially outward of the wall 102. In such embodiments, at least a portion of the head 932 can overlap at least a portion of the wall 104 along the axial direction X of the access member 102 (and thus also along the longitudinal direction L of the retractor 2) when the retractor 2 is attached to the access member wall 104. Thus, the protrusions 920 and the openings 922 can be cooperatively configured to resist inadvertent detachment of the retractor 2 from the access member wall 104 along the transverse direction T.

In other embodiments, as shown in FIG. 9C, the openings 922 can extend from the inner wall surface 116 and terminate at a location radially inward of the outer wall surface 114. In such embodiments, the opening 922 can include an axial receptacle 934 configured to receive a portion of the mating head 932, such that at least a portion of the head 932 overlaps at least a portion of the wall 104 along the axial and longitudinal directions X, L, respectively, as above. It should be appreciated that other complimentary protrusion 920 and opening 922 geometries for providing sturdy, selective attachment of the retractor 2 to the access member wall 104 are within the scope of the present disclosure. It should also be appreciated that in other embodiments the protrusions 920 can extend inwardly from the inner wall surface 116 of the access member 102 and the openings 922 can be defined in the retractor body 3.

In a surgical procedure using the surgical access system 100 of the present embodiment, the physician can insert the retractor body 3 through the working channel 106 to engage and retract soft tissue. Once the soft tissue is engaged, the physician can manipulate the proximal end 4 of the retractor 2 to pull the soft tissue toward the wall 104. In particular, the physician can identify the column 926 of openings 922 in the inner wall surface 116 that is in substantial radial alignment with the desired direction of retraction for coupling with the protrusions 920 of the retractor 2. The physician can then insert the protrusions 920 of the retractor 2 within the select openings 922 of the column 926 at the desired longitudinal position of the retractor 2 relative to the access member 102, thereby affixing the retractor 2 to the inner wall surface 116 at the select circumferential and longitudinal positions of the inner wall surface 116. It should be appreciated that multiple retractors 2 can be affixed to the inner wall surface 116 in like manner for retracting soft tissue as needed.

Referring now to FIGS. 9D and 9E, an additional embodiment is shown in which one or more protrusions 920 extend proximally from a proximal surface 111 of the access member 102. The proximal surface 111 can define the proximal end 110 of the access member 102. In such embodiments, the one or more protrusions 920 can include a plurality of protrusions 920 spaced circumferentially from one another along the proximal surface 111. The proximal surface 111 can be defined by a flange 113 at the proximal end 110 of the access member 102. In the present embodiment, the retractor body 3 defines one or more openings 922 extending therethrough from the inner surface 10 to the outer surface 12. Particularly, the retractor body 3 of the present embodiment can be either pre-bent or bendable such that a first or proximal portion 3a of the retractor body 3 is angularly offset relative to a second or distal portion 3b of the retractor body 3, as described above with reference to FIG. 1C. The proximal portion 3a defines at least one opening 922 that extends along the axial direction X and can thus be mated with a select one of the protrusions 920 for attaching the retractor body 3 to the associated select circumferential portion of the access member 102. As shown, the proximal and distal portions 3a, 3b of the retractor body 3 can be angularly offset from each other in the L-T plane, such that the distal portion 3b extends through the working channel 106 substantially along the axial direction X while the proximal portion 3a is elongate along the radial direction R (or at least along a direction having a directional component along the radial direction R).

In embodiments where the retractor body 3 is pre-bent, the proximal portion 3a defines a single opening 922. In embodiments where the retractor body 3 is bendable, the retractor body 3 can define a plurality of openings 922 spaced in series along the longitudinal direction L, allowing the physician to bend the retractor body 3 at a select longitudinal location to define the respective lengths of the proximal and distal portions 3a, 3b, thereby defining the insertion depth of the distal portion 3b when attached to the retractor body 3. It should be appreciated that, as above, the protrusions 920 can have a stem 930 and a head 932, and can be cooperatively configured with the opening 922 so that the head 932 can overlap at least a portion of the retractor body 3 along the radial direction R when the retractor body 3 is attached to the access member 102. Such overlap can increase the sturdiness of attachment between the retractor body 3 and the access member 102.

During use of the embodiment shown in FIGS. 9D and 9E, the physician can identify the protrusion 920 on the proximal surface 111 in substantial radial alignment with the desired direction of retraction for coupling with the opening 922 of the retractor 2. The physician can insert the retractor body 3 through the working channel 106 and engage and retract soft tissue in the radial direction R, bringing the distal portion 3b of the retractor body 3 toward the inner wall surface. In embodiments where the retractor body 3 is pre-bent, the foregoing step also brings the opening 922 in the bent proximal portion 3a into alignment with the selected protrusion 920. In embodiments where the retractor body 3 is bendable, the physician can bend the retractor body 3 at the select longitudinal location to provide the distal portion 3b with the desired axial depth relative to the access member 102. In either embodiment, with the distal portion 3b engaged with soft tissue and moved toward the select circumferential portion of the inner wall surface 116, the physician can move the proximal portion 3a so that the opening 922 receives the select protrusion 920, thereby attaching the retractor body 3 to the access member 102 as desired. It should be appreciated that multiple retractors 2 can be affixed to the access member 102 in like manner for retracting soft tissue as needed.

Referring now to FIGS. 10A and 10B, an attachment device 1014 for the surgical access system 100 can include a flexible wire 1050 that is configured to be inserted into the working channel 106 of the access member 102 in a first or insertion configuration and then deform into a second or deployed configuration for pushing the retractor body 3 against the inner wall surface 116 and securing it thereto. For example, the wire 1050 can be pre-formed into a neutral shape, such as one or more coils, for example, and can then be loaded into an introducer instrument 1070 (also referred to herein as the introducer 1070) that maintains the wire 1050 in the insertion configuration. The introducer 1070, or at least an end portion thereof, can be inserted within the working channel 106, and the wire 1050 can be deployed (i.e., expelled) from the introducer 1070 and into the working channel 106, wherein the wire 1050 elastically deforms from its insertion configuration to the deployed configuration. This deformation can cause the wire 1050 to form one or more coils that extend circumferentially about the inner wall surface 116 and exert a radially outward spring force F that pushes the retractor body 3 securely against the inner wall surface 116 as the wire 1050 attempts to return to its neutral configuration. In other embodiments, the wire 1050 can be configured as a helical spring when in the neutral configuration, and can be further twisted helically so as to reduce its spring diameter when in the insertion configuration. Once inserted to the desired location within the working channel 106, the wire 1050 can be released so as to expand within the working channel 106 to the deployed configuration. It should be appreciated that the wire 1050 can be constructed of a shape-memory material that is also bio-compatible, such as nitinol, by way of a non-limiting example.

The wire 1050 can have a substantially purely coiled shape in the deployed configuration. In other embodiments, as shown in FIGS. 10C and 10D, the wire 1050 can have an alternate shape in the deployed configuration. For example, the wire 1050 can be configured such that when it is in the deployed configuration, the wire 1050 can define a longitudinal portion 1052 configured to engage along the length of the retractor body 3 and one or more arm portions 1054 configured to engage the inner wall surface 116 of the access member 102. It should be appreciated that other deployed configurations are also within the scope of the present disclosure.

The retractor bodies 3 of any of the preceding embodiments can be constructed of bio-compatible materials including metals, polymers, composite materials, or any combination of the foregoing, by way of non-limiting examples.

It should be appreciated that the retractors 2 and attachment devices 14, 314, 414, 714, 814, 914 described above allow selective placement of the retractor 2 relative to the access member 102, including circumferentially and longitudinally, and thus likewise relative to patient anatomy for fine control of soft tissue retraction. Such fine control of soft tissue retraction is particularly beneficial because, among other things, it reduces the need for resection (removal) of soft tissue at the treatment site.

Referring now to FIGS. 11A and 11B, the retractor members 2 of any of the embodiments described above can include at least one sensor 1102 that is electrically conductive and located at or adjacent the distal end 12 of the retractor 2. The sensor 1102 can be employed for neuromonitoring (e.g., for detecting the presence, proximity, health, and/or other attributes of nerve tissue) at the treatment site, such as to navigate the retractor 2 around (e.g., avoid) nerve tissue, to safely retract nerve tissue with the retractor 2, and/or to assess the health of nerve tissue at the treatment site, as more fully described in the '253 Reference. It should be appreciated that the sensor 1102 can include a single sensor or a plurality of sensors. The sensor 1102 can be in electrical communication with an electric lead 1104 that is located at or adjacent the proximal end 10 of the retractor 2 and is configured for transmitting electrical information obtained by the sensor to a control unit 1106, which can employ a processor 1108 for interpreting the electrical information.

As shown in FIG. 11A, in one such embodiment that employs a sensor 1102, the retractor 2 can include a retractor body 3 that is constructed of an electrically conductive material. The retractor 2 can also include an electrically insulative sheath 1110 disposed over a major portion 3i of the retractor body 3. The sheath 1110 can be configured to provide an exposed portion 3j of the retractor body 3 that defines the sensor 1102. The exposed portion 3j can extend from the sheath 1110 to the distal end 12. The sheath 1110 can also be configured to provide another exposed portion 3k of the retractor body 3 that defines the electric lead 1104, which can extend from the sheath 1110 to the proximal end 10. It should be appreciated that, as an alternative to the sheath 1110, the retractor body 3 can be coated with a layer of insulative material, which layer can be formed or finished so as to provide an exposed portion of the retractor body 3 at or adjacent the distal end 12, which exposed portion can define or carry the sensor 1102. The coating can also be configured to provide an additional exposed portion of the retractor body 3, such as at or adjacent the proximal end 12, for providing the electric lead 1104.

As shown in FIG. 11B, in another embodiment that employs a sensor 1102, retractor 2 can include a retractor body 3 that is constructed of an electrically insulative material, and the sensor 1102 can be disposed over or embedded within the retractor body 3 at or adjacent the distal end 12 thereof. The electric lead 1104 can also be disposed over or embedded within the retractor body 3, such as at the proximal end 10 thereof. The retractor 2 can include an electrical transmission element, such as a wire or trace extending along or through the retractor body 3, from the sensor 1102 to the electric lead 1104.

The insulate materials described above can include parylene, silicone rubbers, fluoropolymers, and elastomers, by way of non-limiting examples. It should be appreciated that in other embodiments employing a sensor 1102, the sensor 1102 can be in wireless communication with the control unit 1106 and/or processor 1108.

Referring now to FIGS. 12A through 12E, in yet other embodiments, an attachment device 1214 for the surgical access system 100 can include a tether 1211 extending from the proximal end 4 of the retractor body 3. As shown in FIG. 12A, the retractor body 3 can be carried by an instrument 1200, which can include a distal elongate portion 1205 that extends along the longitudinal direction L and carries the retractor body 3, such as by bracketing the lateral sides of the retractor body 3. The distal elongate portion 1205 is configured for insertion within the access member 102 to engaging soft tissue with the retractor body 3. The retractor body 3 can define a distal mount 1218, such as a hook, which can extend from the outer surface 12 of the retractor body 3. Additionally, the distal mount 1218 can be configured to engage the distal end 112 of the access member 102. Additionally or alternatively, the distal mount 1218 can be configured to selectively engage any of a plurality of slots 1220 defined in the wall 104 of the access member 102, as shown in FIGS. 12D and 12E.

The tether 1211 can be a wire, suture member, string, or cord, by way of non-limiting examples. Alternatively, as shown in FIG. 12C, the tether 1211 can be a band, such as an elastic band. The tether 1211 can be configured to secure to one or more receiving formations 1215 defined by or carried by the access member 102. The receiving formations 1215 can be receptacles, channels, cleats, and the like, which can be defined on or carried by an exterior of the access member 102. Alternatively, as shown in FIG. 12D, the receiving formations 1215 can optionally be defined on or carried by an access member holder 1260 connected to the access member 102. As shown in FIG. 12E, alternatively or in addition to the receiving formations 1215, the tether 1211 can be affixed to the proximal end 110 of the access member 102 with a fastener, such as a spring clip 1270, for example.

Although the disclosure has been described in detail, it should be understood that various changes, substitutions, and alterations can be made herein without departing from the spirit and scope of the invention as defined by the appended claims. For example, features of the various embodiments described herein can be incorporated into one or more and up to all of the other embodiments described herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A retractor member configured for insertion through a channel of an access member and for moving soft tissue at a treatment site accessible through the channel, comprising:
    a body having a proximal end and a distal end spaced from each other along a longitudinal direction, the distal end defining a retractor blade, the body defining a first surface and a second surface opposite each other along a transverse direction substantially perpendicular to the longitudinal direction; and
    an attachment device configured to selectively attach the body to a portion of the access member such that the body is extendable through the channel and is translatable relative to the access member along the longitudinal direction while the body is attached to the portion of the access member;
    wherein the body has a first side and a second side spaced from each other along a lateral direction substantially perpendicular to the longitudinal and transverse directions, and the attachment device extends from at least one of the first and second sides at a longitudinal portion of the body located intermediate the proximal and distal ends, such that the attachment device is configured to reside within the channel for securing the retractor member to an inner surface of the access member, and
    wherein the attachment device comprises a pair of wings each extending circumferentially from the first and second sides, respectively, at the longitudinal portion, wherein the pair of wings are compliant and are configured to be flexed inward toward each other from a neutral configuration to a flexed configuration by the inner surface of the access member when the pair of wings are disposed in the channel, such that a return force of the pair of wings causes the pair of wings to engage the inner surface of the access member so as to attach the body to the portion of the access member.

2. The retractor member of claim 1, wherein, at the longitudinal portion and in a plane orthogonal to the longitudinal direction, the second surface of the body defines a first radius and outer surfaces of the pair of wings define another radius that is greater than the first radius when the pair of wings are in the neutral configuration.

3. The retractor member of claim 1, wherein the attachment device comprises an attachment member separate from the body, at least a portion of the attachment member comprises magnetic material, and the body comprises one or more magnets each configured for selective attachment to the magnetic material of the at least a portion of the attachment member.

4. The retractor member of claim 1, wherein the first surface is arcuate and concave between the first and second sides in a plane orthogonal to the longitudinal direction, and the second surface is arcuate and convex between the first and second sides in the plane.

5. The retractor member of claim 4, wherein at least at one of the proximal and distal ends, the body defines an end portion that is flared, such that the end portion defines a maximum lateral dimension that is greater than a maximum lateral dimension of an adjacent portion of the body that extends from the end portion toward the opposite one of the proximal and distal ends.

6. The retractor member of claim 4, wherein at least at one of the proximal and distal ends, the body defines an end portion that is angularly offset from an adjacent portion of the body that extends from the end portion toward the opposite one of the proximal and distal ends.

7. The retractor member of claim 1, wherein at least a proximal portion of the body is plastically deformable so as to be bent away from a central axis of the access member after the body is attached to the portion of the access member.

8. The retractor member of claim 1, wherein the body includes at least one electrically conductive sensor at the distal end, and the at least one electrically conductive sensor is in electrical communication with an electric lead that is spaced from the at least one electrically conductive sensor and is configured for communicating sensor information obtained by the at least one sensor to a control unit.

9. The retractor member of claim 8, wherein the body is formed of an electrically conductive material, and the retractor member further comprises electrical insulation covering a major portion of the body, wherein the body includes a distal exposed portion at the distal end, the distal exposed portion defines the at least one electrically conductive sensor, the body further includes a proximal exposed portion at the proximal end, and the proximal exposed portion defines the electric lead.

10. The retractor member of claim 8, wherein the body is formed of an electrically insulative material, and the at least one electrically conductive sensor is embedded in the body at the distal end.

11. A system for retracting soft tissue, comprising:
    an access member having a proximal end and a wall that extends from the proximal end to a distal end of the access member, wherein the wall extends about a central axis in a plane orthogonal to the central axis such that an inner surface of the wall defines a channel that extends along an axial direction oriented along the central axis;
    a retractor body having a proximal end and a distal end spaced from each other along a longitudinal direction, the distal end of the retractor body configured to engage soft tissue, the retractor body defining a first surface and a second surface opposite each other along a transverse direction substantially perpendicular to the longitudinal direction; and
    an attachment device coupled to the retractor body, the attachment device comprising a proximal mount and a distal mount configured to respectively mount to the proximal and distal ends of the access member, wherein at least one of the proximal and distal mounts is configured to move between 1) an unlocked configuration in which the proximal and distal mounts are longitudinally spaced from each other by a first distance, and 2) a locked configuration in which the proximal and distal mounts are longitudinally spaced from each other by a second distance less than the first distance, wherein the second distance corresponds to a distance between the proximal and distal ends of the access member along the axial direction.

12. The system of claim 11, wherein the proximal and distal mounts each comprise a hook configured to hook the respective proximal and distal ends of the access member.

13. The system of claim 11, wherein the retractor body is longitudinally translatable relative to the proximal and distal mounts at least when the attachment device is in the locked configuration.

14. The system of claim 11, further comprising an actuator configured to actuate the at least one of the proximal and distal mounts from the unlocked configuration to the locked configuration.

15. The system of claim 14, further comprising an instrument releasably coupled to the attachment device, the instrument comprising:
  a handle extending from a rear end of the instrument to a front end of the instrument; and
  a coupling mechanism at least partially located at the front end of the instrument, the coupling mechanism configured to iterate between 1) a coupled configuration, in which the instrument is rigidly coupled to the retractor body, and 2) a de-coupled configuration, in which the instrument is de-coupled and removable from the retractor body.

16. The system of claim 15, wherein the coupling mechanism is further configured to move the actuator so as to actuate the at least one of the proximal and distal mounts from the unlocked configuration to the locked configuration.

17. The system of claim 15, wherein the proximal mount comprises a mount base and an engagement member, wherein the actuator extends between the mount base and the engagement member and is configured to actuate longitudinal movement of the engagement member relative to the mount base between the unlocked configuration and the locked configuration.

18. The system of claim 17, wherein:
  the actuator comprises a bias mechanism having at least one spring that biases the engagement member away from the mount base in a bias direction along the longitudinal direction so as to actuate the engagement member to the locked configuration;
  the bias mechanism further comprises a return member configured to move the engagement member toward the mount base and into the unlocked configuration in a direction opposite the bias direction; and
  the coupling mechanism comprises a movement member configured move the return member in the direction opposite the bias direction.

19. The system of claim 15, wherein the retractor body comprises an aperture and the coupling mechanism comprises a pin configured to 1) reside within the aperture so as to couple with the retractor member when the coupling mechanism is in the coupled configuration, and 2) move remote from the aperture so as to de-couple from the retractor member when the coupling mechanism is in the de-coupled configured.

20. The system of claim 19, wherein the coupling mechanism includes a button that is connected to the pin and is configured to iterate between a first position, in which the pin resides within the aperture, and a second position, in which the pin is remote from the aperture.

21. The system of claim 15, wherein the actuator is a tensile member configured to selectively apply tension between the proximal and distal mounts so as to actuate the at least one of the proximal and distal mounts.

* * * * *